United States Patent
Hamaguchi et al.

(10) Patent No.: US 11,572,380 B2
(45) Date of Patent: Feb. 7, 2023

(54) SACCHARIDE POLYCONDENSATE, METHOD FOR PRODUCING THE SAME, AND APPLICATION THEREFOR

(71) Applicant: NIHON SHOKUHIN KAKO CO., LTD., Tokyo (JP)

(72) Inventors: Norihisa Hamaguchi, Shizuoka-Ken (JP); Hitoshi Takaguchi, Shizuoka-Ken (JP); Yoshinori Fujimoto, Shizuoka-Ken (JP); Yutaka Kimoto, Shizuoka-Ken (JP); Hirokazu Hirai, Shizuoka-Ken (JP); Masayasu Takada, Shizuoka-Ken (JP)

(73) Assignee: NIHON SHOKUHIN CO., LTD., Tokyo (JP)

( * ) Notice: Subject to any disclaimer, the term of this patent is extended or adjusted under 35 U.S.C. 154(b) by 168 days.

(21) Appl. No.: 16/718,702

(22) Filed: Dec. 18, 2019

(65) Prior Publication Data

US 2020/0123185 A1 Apr. 23, 2020

Related U.S. Application Data

(63) Continuation of application No. 13/997,878, filed as application No. PCT/JP2011/078802 on Dec. 13, 2011, now abandoned.

(30) Foreign Application Priority Data

| Jan. 7, 2011 | (JP) | 2011-002466 |
| Sep. 15, 2011 | (JP) | 2011-202308 |
| Dec. 9, 2011 | (JP) | 2011-270545 |

(51) Int. Cl.
*C07H 3/00* (2006.01)
*A23L 2/60* (2006.01)
(Continued)

(52) U.S. Cl.
CPC ............... *C07H 3/00* (2013.01); *A21D 2/18* (2013.01); *A23C 9/1307* (2013.01);
(Continued)

(58) Field of Classification Search
CPC . A23L 2/60; A23L 33/10; A23L 33/21; A23L 33/25; A23L 2/52; A23L 15/30;
(Continued)

(56) References Cited

U.S. PATENT DOCUMENTS

| 3,766,165 A | 10/1973 | Rennhard |
| 2008/0125568 A1 | 5/2008 | Endo |

FOREIGN PATENT DOCUMENTS

| CA | 2809276 A1 | 7/2008 |
| GB | 1262842 A | 2/1972 |

(Continued)

OTHER PUBLICATIONS

Watanabe et al. JP2003-231694A, cited in an IDS, machine translation , (Year: 2003).*

(Continued)

*Primary Examiner* — Subbalakshmi Prakash
(74) *Attorney, Agent, or Firm* — Hovey Williams LLP

(57) ABSTRACT

An object of the present invention is to provide a method for producing a saccharide polycondensate which is inexpensive and is applicable to a food or beverage product. Disclosed is a method for producing a saccharide polycondensate, which comprises carrying out a saccharide polycondensation reaction in the presence of activated carbon.

14 Claims, 4 Drawing Sheets

(51) Int. Cl.

| | |
|---|---|
| *A23L 2/52* | (2006.01) |
| *A23L 2/56* | (2006.01) |
| *C07H 1/00* | (2006.01) |
| *C12C 5/02* | (2006.01) |
| *A23C 9/13* | (2006.01) |
| *A23G 3/42* | (2006.01) |
| *A23G 9/34* | (2006.01) |
| *A23C 13/12* | (2006.01) |
| *A23G 4/10* | (2006.01) |
| *A23C 9/154* | (2006.01) |
| *A21D 2/18* | (2006.01) |
| *A23L 33/21* | (2016.01) |
| *A23L 15/00* | (2016.01) |
| *A23L 33/10* | (2016.01) |
| *A23L 33/25* | (2016.01) |
| *C12C 11/00* | (2006.01) |

(52) U.S. Cl.
CPC ............ *A23C 9/1544* (2013.01); *A23C 13/12* (2013.01); *A23G 3/42* (2013.01); *A23G 4/10* (2013.01); *A23G 9/34* (2013.01); *A23L 2/52* (2013.01); *A23L 2/56* (2013.01); *A23L 2/60* (2013.01); *A23L 15/30* (2016.08); *A23L 33/10* (2016.08); *A23L 33/21* (2016.08); *A23L 33/25* (2016.08); *C07H 1/00* (2013.01); *C12C 5/02* (2013.01); *C12C 5/026* (2013.01); *C12C 11/003* (2013.01)

(58) Field of Classification Search
CPC .... A23L 2/56; A23G 9/34; A23G 3/42; A23G 4/10; A21D 2/18; A23C 9/1544; A23C 13/12; A23C 9/1307; C12C 5/026; C12C 11/003; C12C 5/02; C07H 3/00; C07H 1/00
USPC .......................................................... 426/16
See application file for complete search history.

(56) References Cited

FOREIGN PATENT DOCUMENTS

| | | | |
|---|---|---|---|
| JP | S62292791 A | 12/1987 |
| JP | H04124196 A | 4/1992 |
| JP | H04312595 A | 11/1992 |
| JP | 10113162 A | 5/1998 |
| JP | 11056336 A | 3/1999 |
| JP | 11146778 A | 6/1999 |
| JP | 2003231694 A | 8/2003 |
| JP | 2009072077 A | 4/2009 |
| JP | 2010222478 A | 7/2010 |
| WO | 9841545 A1 | 9/1998 |
| WO | 2002083739 A1 | 10/2002 |
| WO | 2011091962 A2 | 8/2011 |

OTHER PUBLICATIONS

Nagumo et al. (JP04124196A,) cited in an IDS full translation. (Year: 1992).*
Hasebe (JP2010-222478A) cited in an IDS, machine translation. (Year: 2010).*
Begli et al. WO 2004031202 A2 detailed abstract (Year: 2004).*
English language translation of IPRP dated Jul. 18, 2013 in connection with PCT/JP2011/078802.
Japanese Patent Office; Notification of Reason for Rejection in the matter of JP App. No. 2011-270545; dated Jan. 20, 2012.
Japanese Patent Office; Notification of Reason for Rejection in the matter of JP App. No. 2011-270545; dated Feb. 24, 2012.
European Patent Office, Extended Search Report, Application No. EP 11 85 4694, dated May 9, 2014, 7 pages.
State Intellectual Property Office of People's Republic China, First Office Action and Search Report, Application No. 201180064296.8, dated Oct. 27, 2014.
Brazilian Patent and Trademark Office, Search Report and Technical Examination Report, Application No. BR112013017099-9, dated May 24, 2018, 12 pages.
International Search Report dated Jan. 24, 2012 in connection with PCT/JP2011/078802.
Kizon Tenkabutsu Meibo Shusai Hinmoku List; Ministry of Health and Welfare Seikatsu Eisei Kyokucho Tsuchi Eika No. 56; Heisei 8 Nen 5 Gatsu 23 Nichi; No. 49, 55, 56, 119, 146, 194, 303.
Edye, L.A et al., Activated carbons in sugar and soft drink manufacture, Sugar Industry 2006, vol. 131, No. 12, pp. 834-840, chapter 2.

* cited by examiner

SACCHARIDE POLYCONDENSATE, METHOD FOR PRODUCING THE SAME, AND APPLICATION THEREFOR

CROSS-REFERENCE TO RELATED APPLICATIONS

This application is a continuation of U.S. patent application Ser. No. 13/997,878 filed Aug. 28, 2013, which represents the national stage entry of PCT International Application No. PCT/JP2011/078802 filed on Dec. 13, 2011 and claims the benefit of Japanese Patent Application No. 2011-002466 filed on Jan. 7, 2011, Japanese Patent Application No. 2011-202308 filed on Sep. 15, 2011 and Japanese Patent Application No. 2011-270545 filed on Dec. 9, 2011. The contents of these applications are incorporated herein by reference as if set forth in their entirety.

TECHNICAL FIELD

The present invention relates to a saccharide polycondensate and a method for producing the same, more particularly, to a saccharide polycondensate using activated carbon as a catalyst, and a method for producing the same and an application therefor.

BACKGROUND ART

Carbohydrate is one of three major nutrients and is a nutrient which is indispensable so as to support life, and it is indispensable to ingest carbohydrate so as to maintain biological activity. Upon dawning age of excessive eating, it has been required to control more calories than are necessary from the viewpoint of prevention of obesity as one of main causes of adult diseases. It is most effective way to control the total amount of foods ingested in the case of controlling calories, however, it is not easy to suppress an appetite for high calorie foods such as sweets. It is an effective way to allow foods to contain a "dietary fiber" so as to control calorie intake while satisfying the appetite. There exists the case where sense of distension is imparted through low calorie diet by adding a dietary fiber to a high intensity sweetener as an extender to give a diet sweetener, or adding a dietary fiber as an excipient of spray-dried foods.

There have been used, as the dietary fiber which has hitherto been used in the field of foods, polydextrose which is a polycondensate obtained by mixing a natural product of a hemicellulose fraction extracted from plants, glucose, sorbitol and citric acid or phosphoric acid at a given ratio and polymerizing the mixture at a high temperature under vacuum, pyrodextrin obtained by roasting starch in the presence of hydrochloric acid, and indigestible dextrin obtained by modifying the pyrodextrin with a digestive enzyme and fractionating an enzyme-resistant fraction. A plant extract has a problem because of its extraction efficiency, colorability, and excessively high viscosity in food processing, and the polydextrose and indigestible dextrin are now highly evaluated in the market. The indigestible dextrin simultaneously causes hydrolysis by acid and thermal polycondensation by roasting of starch. In this respect, it is possible to say that the indigestible dextrin is identical to polydextrose in that saccharide is polycondensed by acid and heat to form a high-molecular glucose polymer (polysaccharides). Frequently, such saccharide polycondensation is less likely to be cleaved by a digestive enzyme because of random bond. In that sense, it is considered that a function as a dietary fiber is imparted. In the case of the indigestible dextrin, an attempt is made to increase the dietary fiber content by further modifying the polycondensate with a digestive enzyme and fractionating an enzyme-resistant fraction. In view of costs, there has been required a novel method for producing a polycondensate without requiring fractionation.

An attempt has been made for a long time to synthesize polysaccharides by directly polycondensing monosaccharides. A synthetic method of polysaccharides is roughly classified into a reverse hydrolysis reaction method, a melt method, a solid phase method, and a solvent method. It is considered that, even when using any method, the obtained product is low calorie sugar, which is free from structural regularity and is less likely to be decomposed by various decomposition enzymes as long as monosaccharides are used. Therefore, in the case of using the above-mentioned dietary fiber in foods, materials are digested with a digestive enzyme and a resistant fraction is evaluated and calculated in terms of the dietary fiber content by an enzymatic-gravimetric method, a combination method, or a non-gravimetric method. In the polycondensation method, the reverse hydrolysis reaction method generally causes low yield, and the solvent method requires the removal of the solvent after the reaction. Therefore, both methods are not suited for the method for producing low calorie sugar (dietary fiber) in view of costs. The solid phase method also had a problem in that long reaction time is required and a catalyst is efficiently mixed. In contrast, the melt method, in which saccharide is melted at a temperature of a melting point or higher of the saccharide as a raw material, followed by dehydration polycondensation at a high temperature under vacuum or in an inert gas flow, is advantageous as compared with the above-mentioned methods because of its simple step, but has a problem in view of colorability.

Among these methods, various melt methods at a high temperature under vacuum have been attempted. Limiting to most inexpensive glucose as the raw material, there have been reported, in addition to a method in which melting is carried out without using a catalyst, followed by dehydration polycondensation, a method in which phosphorous acid is used as a catalyst, a method in which a strong acidic resin is used as a catalyst, and a method in which thionyl chloride is used as a catalyst, a method in which inorganic catalysts such as phosphorus trichloride, phosphorus pentachloride, phosphorus pentoxide, concentrated sulfuric acid, metaboric acid, and zinc chloride are used, a method in which organic catalysts such as citric acid, fumaric acid, tartaric acid, and succinic acid are used, and a method in which minerals such as diatomaceous earth and activated clay are used (Patent Literature 1).

Recently, Suzuki et al. have reported that a sugar chain polymer can be prepared by a method in which a fluorinated sugar is used, or a method in which monosaccharides are subjected to a solid phase reaction together with an acid catalyst (phosphoric acid) (Non Patent Literature 1 and Non Patent Literature 2).

CITATION LIST

Patent Literature

Patent Literature 1: Japanese Patent Application Laid-Open Publication No. 2003-231694

Non-Patent Literature

Non-Patent Literature 1: Atsushi Kanazawa, Shohei Okumura and Masato Suzuki, Org. Biomol. Chem., 3, p. 1746-1750 (2005)

Non-Patent Literature 2: Atsushi Kanazawa, Shingo Namiki and Masato Suzuki, Journal of Polymer Science. Vol. 45, p. 3851-3860 (2007)

SUMMARY OF THE INVENTION

Problem to be Solved

However, when considering application of a saccharide polycondensate obtained by saccharide polycondensation to foods, some catalysts and solvents used in the case of polycondensation are not suited for foods. In particular, since a nonvolatile acid is used as a catalyst in any conventional methods except for some methods, a large amount of the catalyst remains in the reaction product, and thus most of these catalysts may be sometimes incorporated into a sugar skeleton by a transesterification reaction. The product may sometimes exhibit sourness because of the remaining catalyst and, in some cases, it was necessary to remove or neutralize an acid catalyst. Furthermore, any saccharide polycondensates obtained by a conventional method had a problem in colorability caused by the decomposition of a raw saccharide.

An object of the present invention is to provide a saccharide polycondensate which is inexpensive and is applicable to a food or beverage product, and a method for producing the same. Another object of the present invention is to provide a food or beverage product having improved taste quality and flavor.

Solution to Problem

Surprisingly, the present inventors have found that it is possible to obtain a saccharide polycondensate, which exhibits low coloration degree and high indigestibility, by carrying out a saccharide polycondensation reaction in the presence of activated carbon. The present inventors have also found that saccharides in general can serve as a substrate of the saccharide polycondensation reaction by activated carbon. The present inventors have further found that the obtained saccharide polycondensate enables masking of bad taste of a high intensity sweetener-containing beverage and imparting of body, and the obtained saccharide polycondensate enables imparting of body to a beer flavored beverage without imparting off-flavor. The present invention is based on these findings.

Specifically, the present invention is as follows.
(1) A method for producing a saccharide polycondensate or a reduced product thereof, which comprises polycondensing one or more saccharides or derivatives thereof in the presence of activated carbon.
(2) The method according to (1), wherein the saccharide is selected from a monosaccharide, an oligosaccharide, and a polysaccharide.
(3) The method according to (1) or (2), wherein a polycondensation reaction is carried out under normal or reduced pressure.
(4) The method according to any one of (1) to (3), wherein the polycondensation reaction is carried out under a temperature of 100° C. to 300° C.
(5) The method according to any one of (1) to (4), wherein a saccharide polycondensate or a reduced product thereof is produced as a saccharide polycondensate composition.
(6) The method according to (5), wherein the content of a dietary fiber in the saccharide polycondensate composition is 30% by weight or more.
(7) A saccharide polycondensate or a reduced product thereof, or a saccharide polycondensate composition, which is produced by the method according to (1) to (6).
(8) A food or beverage product, which is obtained by adding thereto the saccharide polycondensate or the reduced product thereof, or a saccharide polycondensate composition according to (7).
(9) The food or beverage product according to (8), which further comprises a high intensity sweetener.
(10) The food or beverage product according to (9), which is a beverage.
(11) The food or beverage product according to (10), wherein the beverage is a carbonated beverage, an isotonic sport beverage, a beverage containing fruit juice, a coffee beverage, or an alcoholic beverage.
(12) The food or beverage product according to any one of (9) to
(11), wherein the content of a saccharide polycondensate and a reduced product in the food or beverage product is 0.02% to 20% by weight.
(13) The food or beverage product according to (8), which is a beer-flavored beverage.
(14) The food or beverage product according to (13), wherein a saccharide polycondensate or a reduced product thereof, or a saccharide polycondensate composition is added before fermentation and/or during fermentation.
(15) The food or beverage product according to (13), wherein a saccharide polycondensate or a reduced product thereof, or a saccharide polycondensate composition is added after fermentation.
(16) The food or beverage product according to any one of (13) to
(15), wherein the content of a saccharide polycondensate and a reduced product in the food or beverage product is 0.1% to 10% by weight.
(17) A method for producing a beer-flavored alcoholic beverage, which comprises adding the saccharide polycondensate or the reduced product thereof or the saccharide polycondensate composition according to (7) to a wort or an unfermented liquid to carry out fermentation.
(18) A method for producing a beer flavored alcoholic beverage, which comprises adding the saccharide polycondensate or the reduced product thereof, or the saccharide polycondensate composition according to (7) to a fermented liquid.
(19) A livesock feed, which is obtained by adding thereto the saccharide polycondensate or the reduced product thereof, or the saccharide polycondensate composition according to (7).

In the method for producing a saccharide polycondensate of the present invention, activated carbon is used as a catalyst. The activated carbon can be easily removed outside the system by a solid-liquid separation, and safety is recognized for use in foods, as the activated carbon is used as food additives. Therefore, according to the present invention, it is possible to simply produce a saccharide polycondensate, which is applicable to a food or beverage product as it is, at a low price.

According to the method for producing a saccharide polycondensate of the present invention, it is also possible to produce a saccharide polycondensate, which has low coloration and is enriched with a dietary fiber fraction, in a single stage. Since the activated carbon can be removed outside the system by solid-liquid separation after the reaction, the saccharide polycondensate thus produced is neutral or weak acid and does not exhibit sourness. Therefore, the saccharide polycondensate produced by the production method of the present invention is useful as a dietary fiber which is usable as a substitute of saccharide in a food or beverage product.

According to the method for producing a saccharide polycondensate of the present invention, it is also possible to use a hydrol, which is a centrifuged liquid formed in the case of producing a crystalline glucose, as a substrate of a saccharide polycondensation reaction. Since the hydrol contains impurities and moisture in a large amount as compared with a crystalline glucose, the coloration degree increases and flavor is impaired in the reaction method using a conventional acid catalyst such as hydrochloric acid or citric acid, and thus it was not preferred to use the hydrol. Namely, the production method of the present invention is advantageous from the viewpoint of recycling and reduction in costs of raw materials since it is possible to produce a dietary fiber, which is applicable to a food or beverage product, by using the hydrol which becomes industrial wastes.

DETAILED DESCRIPTION OF THE INVENTION

Figure 1:
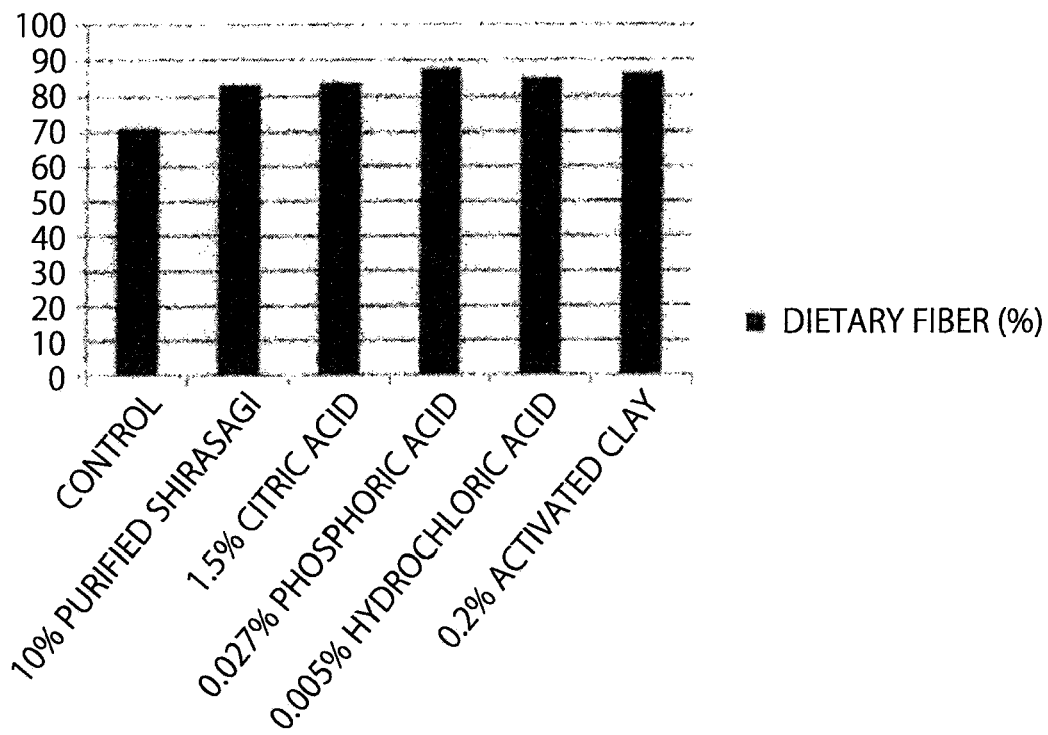
FIG. 1 is a diagram showing the content of a dietary fiber in a saccharide polycondensate in case where activated carbon is used as a catalyst, and citric acid, phosphoric acid, hydrochloric acid, and activated clay are used as catalysts, in a saccharide polycondensation reaction.

Saccharide Polycondensate and Method for Producing the Same

In the production method of the present invention, a saccharide polycondensation reaction is carried out in the presence of activated carbon. Here, "saccharide polycondensation reaction" refers to a reaction in which saccharides mutually undergo polycondensation polymerization to obtain a saccharide polycondensate, and typically refers to a reaction in which hydroxyl groups of saccharide mutually undergo dehydration polycondensation.

In the present invention, the saccharide polycondensation reaction can be carried out by using one or more kinds of saccharides as substrates.

The saccharide, which can be allowed to undergo a saccharide polycondensation reaction, is not specifically limited, and it is possible to use any of monosaccharide, oligosaccharide, and polysaccharide, and a reduced product thereof. When it is intended to use the thus produced saccharide polycondensate in a food or beverage product, it is possible to use saccharide which can be used as a food or beverage product.

In the present invention, a derivative of saccharide can also be used as a substrate of a saccharide polycondensation reaction. Examples of the derivative of saccharide include oxides such as saccharic acid; reduced products such as sugar alcohol; and modified products such as amino sugar, etherified sugar, halogenated sugar, and phosphorylated sugar. When it is intended to use the thus produced saccharide polycondensate in a food or beverage product, it is possible to use a derivative which can be used as a food or beverage product. Examples thereof include sorbitol, galactitol, mannitol, xylitol, erythritol, maltitol, lactitol, glucosamine, glucose-6-phosphoric acid and the like, and there is no specific limitation as long as it is a saccharide derivative which can be used as a food or beverage product.

In the present invention, the expression "monosaccharide" refers to a saccharide which composes a structural unit of an oligosaccharide or a polysaccharide, and examples thereof include glucose, galactose, mannose, ribose, arabinose, xylose, lixose, erythrose, furactose, psicose and the like. There is no specific limitation as long as it is monosaccharide which can be used as a food or beverage product.

In the present invention, the expression "oligosaccharide" refers to a saccharide in which 2 to 10 monosaccharides are linked together, and examples thereof include maltose, cellobiose, trehalose, gentiobiose, isomaltose, nigerose, sophorose, kojibiose, sucrose, turanose, lactose, xylobiose, maltooligosaccharide, isomaltooligosaccharide, xylooligosaccharide, cyclodextrin and the like. There is no specific limitation as long as it is saccharide which can be used as a food or beverage product.

In the present invention, the expression "polysaccharide" refers to a saccharide in which 11 or more monosaccharides are linked together, and examples thereof include starch, dextrin, pullulan, dextran, arabinoxylan, pectin, inulin, galactan, mannan, indigestible dextrin, polydextrose and the like. There is no specific limitation as long as it is a saccharide which can be used as a food or beverage product.

In the production method of the present invention, saccharides in general can serve as a substrate of a saccharide polycondensation reaction by activated carbon, and examples of the saccharide, which can be used as a polycondensation substrate, include glucose, and a combination of gluclose and one or more kinds selected from the group consisting of a monosaccharide other than glucose, a reduced product of glucose, an oligosaccharide, and a dextrin. In addition, one or more kinds of a monosaccharide other than glucose, an oligosaccharide, and a polysaccharide may be used in combination and used as the substrate of the saccharide polycondensation reaction. It is also possible to use starch hydrolysate as the substrate of the saccharide polycondensation reaction.

In the production method of the present invention, the substrate of the saccharide polycondensation reaction may be a crystallized saccharide and/or a non-crystalline saccharide powder, or a syrup-like saccharide. The syrup-like saccharide, which can be used as the substrate of the saccharide polycondensation reaction in the production method of the present invention, is not specifically limited as long as it is an aqueous solution of saccharide, and it is preferred that it has low moisture content in a polycondensation reaction.

In the production method of the present invention, the saccharide polycondensation reaction can be carried out at 100° C. or higher, and preferably a temperature which is a melting point or higher of saccharide serving as the substrate. From the viewpoint of reaction efficiency, the saccharide polycondensation reaction can be carried out at a temperature in a range of 100° C. to 300° C., preferably 100° C. to 280° C., and more preferably 170° C. to 280° C. The reaction time can be adjusted in accordance with the degree of polycondensation reaction progress. In case where the reaction time is adjusted so that a ratio of an indigestible fraction in the reaction product becomes 75% or more, for example, the conditions are as follows: 5 to 180 minutes at a reaction temperature of 180° C., 1 to 180 minutes at a reaction temperature of 190° C., and 1 to 180 minutes at a reaction temperature of 200° C. The structure of the reactor varies depending on a normal or reduced pressure type, and there is no specific limitation as long as it is a reactor which satisfies the heating condition of 100° C. to 300° C. Examples thereof include a tray hot air dryer, a thin film evaporator, a flush evaporator, a vacuum dryer, a hot air dryer, a steam jacket screw conveyer, a drum dryer, an extruder, a worm shaft reactor, a kneader and the like. It is also possible to use a continuous reactor.

In the production method of the present invention, the saccharide polycondensation reaction can be carried out under normal pressure or vacuum condition. It is advantageous to carry out the saccharide polycondensation reaction under vacuum condition since the coloration degree of the reaction product decreases.

It is possible to use, as "activated carbon" used in the production method of the present invention, those which are known as a porous carbonaceous adsorbent. The activated carbon can be obtained by mainly carbonizing natural carbonaceous materials derived from animals and plants as well as minerals, such as coal, coke, pitch, bone charcoal, charcoal, coconut shell, lumber, sawdust, lignin, and beef bone; organic polymers, for example, synthetic resins such as phenol resin and polyacrylonitrile; and carbonaceous materials such as soot through a heat treatment, followed by deactivation.

The "activated carbon" used in the present invention may be either activated carbons themselves or articles partially containing activated carbons. Such activated carbons can be, for example, activated carbon supported on a support such as a plastic, a mineral, a ceramic, or a fiber; granulated article prepared by granulating powdered activated carbon with a binder; and a granulated article of powdered activated carbon with a powder typically of a mineral or a ceramic. Some materials such as bone charcoal, wood charcoal, graphite, and carbon black may partially contain activated carbons in the structure.

The "activated carbon" used in the present invention may be those obtained by derivatizing the activated carbon. For example, it is possible to use activated carbon in which carboxyl groups are introduced by an oxidation reaction treatment with hydrogen peroxide or nitric acid, and activated carbon in which sulfone groups are introduced by a sulfonation treatment with sulfuric acid or fuming sulfuric acid.

The shape of the activated carbon used in the present invention is not specifically limited, and examples thereof include granular, powdery, fibrous, sheet-like, or honeycomb-like shape. Specific examples of the activated carbon used in the present invention include powdered activated carbons such as steam activated carbon and zinc chloride carbon; and granular activated carbons such as crushed activated carbon, granulated activated carbon, pelletized activated carbon, and spherical activated carbon.

When using the powdered activated carbon as the activated carbon used in the present invention, for example, it is possible to use "Shirasagi A, Shirasagi C, and Purified Shirasagi" manufactured by Japan EnviroChemicals, Ltd. When using the granular activated carbon, for example, it is possible to use "Granular Shirasagi WH and Granular Shirasagi C" manufactured by Japan EnviroChemicals. Ltd.; "F400, F300, PCB, BPL, CAL, CPG, and APC" manufactured by Toyo Carbon Co., Ltd.; "Kuraray Coal KW" manufactured by KURARAY CHEMICAL CO., LTD.; "BAC" manufactured by KUREHA CHEMICAL INDUSTRY CO., LTD.; and "PN, ZN, SA, SA-SW, SX, CA, CN, CG, D-10, W, GL, and HB PLUS" manufactured by Norit Japan Co., Ltd. When using the fibrous activated carbon, it is possible to use "FX-300" manufactured by Toyo Rayon Co., Ltd.; "M-30" manufactured by Osaka Gas Co., Ltd.; and "KF-1500" manufactured by TOYOBO CO., LTD. When using the sheet-like activated carbon, it is possible to use "Microlite AC" manufactured by Kanebo, Ltd.

The amount of the activated carbon used in the production method of the present invention is not specifically limited as long as the saccharide polycondensation reaction proceeds, and can be adjusted in a range of preferably 0.01 to 100 parts by weight, and more preferably 0.1 to 10 parts by weight, based on 100 parts by weight of a saccharide including glucose.

Unlike a conventional metal catalyst and an acidic catalyst, the activated carbon is particularly suited for use in foods because of its less risk in view of sanitation and high safety in handling, or even when it remains in the product. The activated carbon can be easily separated from the reaction system by sedimentation, filtration, centrifugation, or use of a packed column. When using a conventional acid catalyst, an acid catalyst may be sometimes bound in the structure of the saccharide polycondensate or remain in the product, and thus making it difficult to completely separate the catalyst. However, the activated carbon of the present invention can be easily separated after the reaction.

The activated carbon is excellent in reusability, and is also preferred in view of economy since it is excellent in reusability and can be repeatedly used. The reuse method of the activated carbon of the present invention can be an existing method and is not specifically limited. For example, it is possible to use a vacuum regeneration method in which an adsorbate is desorbed by decreasing solute concentration of a solvent and pressure; a solvent regeneration method of extracting with a solvent; a substitution regeneration method of substituting with the other adsorbate; a heat desorption method by heating; a chemical regeneration method by a heat treatment; and an oxidative decomposition regeneration method by oxidation and decomposition.

In the production method of the present invention, the saccharide polycondensation reaction may be carried out by using, in addition to the activated carbon, a saccharide polycondensation reaction catalyst other than the activated carbon. Examples of the saccharide polycondensation reaction catalyst, which can be used together with the activated carbon, include an acid catalyst, and specific examples thereof include inorganic acid catalysts such as hydrochloric acid, sulfuric acid, and phosphoric acid; and organic acid catalysts such as citric acid, fumaric acid, maleic acid, adipic acid, tartaric acid, succinic acid, and malic acid. It is also possible to use, in addition to the acid catalyst, solid catalysts such as activated clay, diatomaceous earth, platinum, and ion-exchange resin. From the viewpoint capable of using as a food or beverage product and a food supplement, and simply removing a catalyst from the reaction system, the catalyst is preferably a nonvolatile catalyst, and more preferably a nonvolatile solid catalyst.

The saccharide polycondensate obtained by the production method of the present invention may be converted into a sugar alcohol. In the present invention, the sugar alcohol refers to a sugar alcohol in which aldehyde groups of reducing terminal glucosyl groups of saccharide are reduced into hydroxyl groups.

The method of obtaining the sugar alcohol is well-known to those skilled in the art and examples of usable reduction method include a method using a hydride reducing agent, a method using metal in a protonic solvent, an electrolytic reduction method, a catalytic hydrogenation reaction method and the like. In the present invention, when a small amount of a sugar alcohol is prepared, the method using a hydride reducing agent is convenient since it does not require a simple and special device. In contrast, when the production is carried out in an industrial large scale, the method using a catalytic hydrogenation reaction is preferable in view of excellent economy and less by-products.

The catalytic hydrogenation reaction is a reaction in which hydrogen is added to a double bond moiety of an unsaturated organic compound in the presence of a catalyst, and is also generally called a hydrogenation reaction. Describing specifically the method for producing a sugar alcohol according to the present invention, a saccharide polycondensate used in the present invention is dissolved in water and a moderate amount of a Raney nickel catalyst is added thereto, and then a hydrogen gas is added thereby reducing under a high temperature condition. Then, the reduced product is subjected to a decolorization and deionization treatment to obtain a composition of a reduced product of a saccharide polycondensate.

The catalyst, which can be used in the catalytic hydrogenation reaction, is not specifically limited as long as it is a known hydrogenation catalyst, and examples thereof include nickel catalysts such as a nickel-carrier catalyst, obtained by supporting on various carries such as Raney nickel, reduced nickel, diatomaceous earth, alumina, pumice, silica gel, and acid clay; cobalt catalysts such as Raney cobalt, reduced cobalt, and cobalt-carrier catalysts; copper catalysts such as Raney copper, reduced copper, and copper-carrier catalysts; palladium catalysts such as palladium black, palladium oxide, colloidal palladium, palladium-carbon, palladium-barium sulfate, palladium-magnesium oxide, and palladium-alumina catalysts; platinum catalysts, for example, platinum-carrier catalysts such as platinum black, colloidal platinum, platinum oxide, platinum sulfide, and platinum-carbon catalysts; rhodium catalysts such as colloidal rhodium, rhodium-carbon, and rhodium oxide catalysts; platinum group catalysts such as a ruthenium catalyst; rhenium catalysts such as rhenium oxide and rhenium-carbon catalysts; copper chromium oxide catalysts; molybdenum trioxide catalysts; vanadium oxide catalysts; tungsten oxide catalysts; and silver catalysts. Among these catalysts, Raney nickel, reduced nickel, and nickel diatomaceous earth catalysts are preferably used, and a Raney nickel catalyst is more preferably used.

The pressure of hydrogen is usually in a range of 10 to 250 kg/cm$^2$, and preferably 50 to 200 kg/cm$^2$. The reaction temperature varies depending on the amount of the catalyst and the kind of the solvent, and is preferably in a range of 80 to 200° C., and more preferably 90 to 160° C.

In the production method of the present invention, it is possible to produce a saccharide polycondensate composition in which the content of the dietary fiber is 30% by weight or more, preferably 50% by weight or more, and more preferably 75% by weight or more. The dietary fiber content can be measured in accordance with an analytical method defined in Eishin No. 13. It is possible to provide a saccharide polycondensate having controlled molecular weight and viscosity by controlling the composition of saccharide and the reaction conditions. For example, when preparing using sorbitol and glucose in combination, it is possible to obtain a water-soluble dietary fiber having low molecular weight and low viscosity as compared with a water-soluble dietary fiber prepared by using glucose alone, since sorbitol molecules function as reaction stopping molecules. In contrast, when using a high molecular weight material such as oligosaccharide or dextrin in combination with glucose, it is possible to obtain a water-soluble dietary fiber having higher molecular weight and high viscosity. When preparing using arabinose and xylose, it is possible to obtain a water-soluble dietary fiber having higher molecular weight as compared with a water-soluble dietary fiber prepared by using glucose. It becomes possible to produce a saccharide polycondensate, which is categorized as oligosaccharide, by decreasing the reaction time. In such way, the molecular weight and viscosity of the saccharide polycondensate can be controlled by a combination of saccharide, kinds of saccharide and reaction conditions.

The coloration degree of a saccharide polycondensation composition produced by the production method of the present invention varies depending on the kind of the saccharide substrate and reaction condition to be used, and absorbance at 420 nm ($OD_{420}$) in an aqueous 20% (w/w) solution can fall in a rage of 0 to 10.0 (and preferably in a range of 0 to 5.0). When glucose is used alone as the saccharide substrate, the coloration degree of a saccharide polycondensation composition produced by the production method of the present invention can fall in a range of 0 to 2.0 in terms of an absorbance at 420 nm ($OD_{420}$) in an aqueous 20% (w/w) solution.

In the production method of the present invention, a high molecular weight polysaccharide can be synthesized by using, as a starting material, glucose composing a basic structural unit of saccharide. In the production method of the present invention, the saccharide polycondensation reaction can be carried out by using not only glucose purified products such as anhydrous and/or hydrous crystalline glucoses and a non-crystalline powdered glucose product, but also a glucose syrup. In particular, as shown in below-mentioned Examples, it is possible to use, as a polycondensation substrate, a glucose syrup such as hydrol formed in a glucose purification step, and thus the production method of the present invention is extremely advantageous from the viewpoint of recycling and reduction in costs of raw materials.

In the production method of the present invention, a high molecular weight polysaccharide can be synthesized by using a saccharide other than glucose as a starting material. In such way, when polycondensation is carried out by allowing glucose to coexist with a saccharide other than glucose, it is advantageous in that a heterosaccharide polycondensate with the composition closer to that of a natural dietary fiber derived from plants can be obtained.

In the production method of the present invention, the composition of the saccharide polycondensate obtained by a polycondensation reaction can be added to a food or beverage product as it is, and the product obtained by the polycondensation reaction may be optionally centrifuged or filtered to remove insolubles, followed by concentration of a water-soluble fraction to give a solution containing a saccharide polycondensate. Alternatively, the product may be optionally concentrated after decoloration by activated carbon or removal of an ionic component by a proper ion-exchange resin. In storage stability and subsequent use, the product is preferably concentrated until achieving water activity enough to prevent the growth of microorganism after decolorization or removal of ions. Alternatively, the product can be dried to form powders so as to make it easy to use according to the intended use. Usually, a freeze drying, spray drying or drum drying method can be used for drying. It is desired that the dry matter is optionally crushed to form dry powders.

The dry matter of the saccharide polycondensate produced by the production method of the present invention exhibits remarkably excellent solubility in water or an alcohol solution, as compared with a commercially available water-soluble dietary fiber such as indigestible dextrin or polydextrose (Example A12). Therefore, it is advantageous in that the time required to dissolve the dry matter in water can be decreased and thus improving production efficiency when various food or beverage products (especially, the below-mentioned beverage or beer flavored beverage containing a high intensity sweetener) are produced by using the dry matter of the saccharide polycondensate produced by the production method of the present invention.

The product obtained by the production method of the present invention contains a saccharide with the polymerization degree of less than 3, such as glucose, maltose or gentiobiose, together with a saccharide polycondensate with the polymerization degree of 3 or more. This product can be used in the below-mentioned food or beverage product as it is, and these components may be optionally removed. Means well-known to those skilled in the art may be used as an isolation and purification method of saccharide and a separation and removal method of saccharide, and it is possible to use purification methods of saccharide, which are well-known to those skilled in the art, such as membrane separation, gel filtration chromatography, carbon-Celite column chromatography, and strong acidic cation-exchange column chromatography.

When the product obtained by the production method of the present invention is used for improvement in flavor of a food or beverage product, or masking of harsh unpleasant taste of pharmaceuticals and calorie control, the product may contain a saccharide or a branched saccharide with the polymerization degree of less than 3. In view of balance of taste and calorie, a saccharide with the polymerization degree of less than 3 may be partially or entirely separated and removed by well-known methods such as membrane separation, gel filtration chromatography, carbon-Celite column chromatography, and strong acidic cation-exchange column chromatography.

Furthermore, when the product obtained by the production method of the present invention is used for an improvement in flavor of a food or beverage product and calorie control, enzymatic modification may be carried out in view of calorie reduction and balance of taste quality. It is also possible to carry out separation and removal of the above saccharide before and after enzymatic modification. In such an enzymatic modification method, one or more kinds of enzymes can be used in combination. In the enzymatic modification method, a plurality of enzymes may be reacted stepwise or simultaneously.

The enzyme used in the above enzymatic modification is not specifically limited, and examples thereof include α-amylase, β-amylase, glucoamylase, isoamylase, pullulanase, amyloglucosidase, cyclodextringlucanotransferase and the like. Furthermore, commercially available products of these enzymes are exemplified, preferably.

Application to Food or Beverage Product

It was confirmed that when the saccharide polycondensate produced by the production method of the present invention, and a reduced product and a saccharide polycondensate composition thereof are added to a food or beverage product, a dietary fiber can be given without impairing appearance and flavor of the food or beverage product (see below-mentioned Examples D1 to D25). Namely, according to the present invention, there is provided a dietary fiber-reinforced food or beverage product, containing a saccharide polycondensate produced by the production method of the present invention, and a reduced product and a saccharide polycondensate composition thereof added therein.

"Food or beverage product" in the present invention may be any food or beverage product. Examples of the food or beverage product, to which a saccharide polycondensate produced by the production method of the present invention, and a reduced product and a saccharide polycondensate composition thereof can be added, include various seasonings such as soy sauce, powdered soy sauce, miso (soybean paste), powdered miso (soybean paste), moromi (unrefined soy), fish sauce (made from fermented salted fish), rice seasoning, mayonnaise, dressing, vinegar, sanbaizu (mixture of vinegar, soy sauce and sugar), powdered sushi vinegar, Chinese seasoning, thin dipping sauce for tempura, noodle soup, Worcester sauce, ketchup, sauce for barbecued meat, curry roux, stew mix, soup stock, Japanese bouillon, compound seasoning, mirin (sweet sake used as seasoning), boiled-down mirin (sweet sake used as seasoning), table sugar, and coffee sugar; various Japanese confectioneries such as rice cracker, cubic rice crackers, millet brittle, Turkish delight, mochi (rice cakes), bun with bean-jam filling, sweet rice jelly, bean jams, chunky sweet bean jelly, soft chunky sweet bean jelly, Kingyoku (literally, brocade balls), jelly, Kasutera sponge cake, and candy; various Western confectioneries such as bread, biscuit, cracker, cookie, pie, purine, buttercream, custard cream, shoe cream, waffle, sponge cake, donut, chocolate, chewing gum, caramel, nougat, and candy; ices such as ice cream and sherbet; syrups such as fruits preserved in syrup, and syrup for shaved ice; pastes such as flower paste, peanut paste, and fruit paste; processed foods of fruits and vegetables, such as jam, marmalade, food preserved in syrup, and candied fruit; Japanese pickles such as sliced vegetables pickled in soy sauce, pickled daikon (Japanese radish), and pickles of sliced turnip; seasonings for Japanese pickles, such as seasoning for pickled daikon (Japanese radish), and seasoning for Chinese cabbage pickles; meat products such as ham and sausage; fish meet products such as fish meat ham, fish meat sausage, boiled fish paste, tube-shaped fish paste cake, and deep-fried fish ball; various delicacies such as salted fish entrails of sea urchin and squid, vinegared kelp, dried seasoned tore squid, and mashed and seasoned fish of codfish, sea bream and shrimp; deli foods such as Tsukudani preserved food in soy sauce made from laver, edible wild plants, dried squid, small fish, and shellfish, cooked beans, fish boiled in broth, potato salad, and kobu maki (kelp roll); instant foods such as dairy products, fish meet, bottled products of meat, fruits and vegetables, canned products, pudding mix, pancake mix, instant juice, instant coffee, instant azuki-bean soup with rice cake, and instant soup; frozen foods; fruit and vegetable beverages, such as a beverage containing fruit juice, fruit juice, and vegetable juice; carbonated beverages such as cider and ginger ale; isotonic sport beverage coffee beverages such as isotonic beverage and amino acid beverage; tea-based beverages such as green tea; milk-based beverages such as lactic acid beverage and cocoa; alcoholic beverages such as Japanese spirit with soda, refined sake, and fruit liquor; energy drink; and baby food, therapeutic food, liquid food, drinkable preparation, and peptide foods.

The content of the saccharide polycondensate in a food or beverage product in the present invention is not specifically limited, and can be adjusted to 0.01 to 99% by weight, preferably 0.01 to 50% by weight, and more preferably 0.1 to 30% by weight, in terms of the solid content from the viewpoint of effectively giving a dietary fiber to the food or beverage product.

To the food or beverage product of the present invention, in addition to a saccharide polycondensate produced by the production method of the present invention, or a reduced product or a saccharide polycondensate composition thereof, one or more kinds of other water-soluble dietary fibers may be added. Examples of the other water-soluble dietary fiber include indigestible dextrin, polydextrose, soybean-derived water-soluble dietary fiber, hydrolyzed guar gum, glucomannan, inulin, pectin, sodium alginate and the like.

The food or beverage product of the present invention may be those which are sold at a normal temperature, sold in a warmed state, sold in a chilled state, or sold in a frozen state, and can be produced by a conventional method, except for allowing to contain a saccharide polycondensate produced by the production method of the present invention, or a reduced product or a saccharide polycondensate composition thereof. It is possible to optionally add, in addition to the above-mentioned components, a saccharide, a protein, an amino acid, fats and oils, an emulsifier, a pigment, a flavoring agent, a juice, puree, a sour agent, a seasoning, an antioxidant, a preservative, an extract, a starch adhesive, a thickener, a pH adjustor, liquors, vitamins, and minerals.

In the food or beverage product of the present invention, it is possible to use, as a powdered base, a saccharide polycondensate produced by the production method of the present invention, or a reduced product or a saccharide polycondensate composition thereof. It is possible to obtain a green tea extract powder, which is excellent in solubility and contains a dietary fiber given moderately, by adding a saccharide polycondensate of the present invention to a green tea extract liquid such as green tea, followed by spray drying. The saccharide polycondensate of the present invention does not impair flavor of a food or beverage product to be powdered even when used as a powdered base, and is advantageous in this respect.

In the food or beverage product of the present invention, it is possible to use, as a dietary fiber reinforcer, a saccharide polycondensate produced by the production method of the present invention, or a reduced product or a saccharide polycondensate composition thereof. Such a dietary fiber reinforcer can be used by adding so as to meet each customer's taste in case of cooking. For example, in the case of cooking grains such as rice, wheat variety, and millet, the saccharide polycondensate of the present invention is added, followed by rice cooking, and thus making it possible to obtain dietary fiber-enriched cooked rice. Use of the saccharide polycondensate of the present invention in rice cooking is advantageous in that not only a dietary fiber can be added without exerting an adverse influence on flavor of the obtained cooked rice, but also cooked rice per se becomes easy to be loosened, and thus improving loosening properties of cooked rice.

Application to High Intensity Sweetener-Containing Food or Beverage
Product

Since a high intensity sweetener has high sweetness and low calorie as compared with sucrose, use for a non-sugar product and a zero calorie product has been intensively examined. However, the high intensity sweetener is inferior in taste quality as compared with sucrose, and had a problem that it causes peculiar aftertaste and bad taste, and lacks of body as compared with sucrose. Furthermore, it is pointed out that use of a high intensity sweetener causes elimination of peculiar swallowness and cool sensation in a beverage, and a beverage with satisfactory taste quality had not yet obtained.

As one of solutions to these problems, there has been developed technology in which various water-soluble dietary fibers are added to a food or beverage product using a high intensity sweetener. It is known that polydextrose or indigestible dextrin, which is a sort of water-soluble dietary fibers, has the masking effect of a high intensity sweetener (see Foods and Developments, Vol. 5, No. 2, pp. 53-56).

However, technology using these water-soluble dietary fibers does not sufficiently reduce bad taste of a high intensity sweetener and impart body, and a satisfactory high intensity sweetener-containing food or beverage product had not yet obtained.

It was confirmed that when a saccharide polycondensate produced by the production method of the present invention, and a reduced product and a saccharide polycondensate composition thereof is added to a food or beverage product containing a high intensity sweetener, it imparts body to a high intensity sweetener lacking the body, and also enables masking of bad taste caused by a high intensity sweetener (see below-mentioned Examples B1 to B8). Namely, according to the present invention, there is provided a high intensity sweetener-containing food or beverage product, containing a saccharide polycondensate produced by the production method of the present invention, and a reduced product and a saccharide polycondensate composition thereof added therein. The high intensity sweetener-containing food or beverage product of the present invention is advantageous in that it has operation and effect capable of imparting body and masking bad taste caused by a high intensity sweetener, and is also capable of efficiently digesting a dietary fiber.

The high intensity sweetener used in the present invention is not specifically limited as long as it is a high intensity sweetener which can be used in a food or beverage product, and examples thereof include one or more kinds selected from sucralose, aspartame, acesulfame potassium, stevia, α-glucosyltransferase-treated stevia, thaumatin, saccharin, saccharin sodium, cyclamate, neotame, and alitame. One or more kinds selected from sucralose, aspartame, acesulfame potassium, stevia, α-glucosyltransferase-treated stevia, and neotame are more preferable.

The "food or beverage product containing a high intensity sweetener" in the present invention may be any food or beverage product as long as it is a food or beverage product containing a high intensity sweetener. Specific examples thereof include various seasonings such as soy sauce, powdered soy sauce, miso (soybean paste), powdered miso (soybean paste), moromi (unrefined soy), fish sauce (made from fermented salted fish), rice seasoning, mayonnaise, dressing, vinegar, sanbaizu (mixture of vinegar, soy sauce and sugar), powdered sushi vinegar, Chinese seasoning, thin dipping sauce for tempura, noodle soup, Worcester sauce, ketchup, sauce for barbecued meat, curry roux, stew mix, soup stock, Japanese bouillon, compound seasoning, mirin (sweet sake used as seasoning), boiled-down mirin (sweet sake used as seasoning), table sugar, and coffee sugar; various Japanese confectioneries such as rice cracker, cubic rice crackers, millet brittle, Turkish delight, mochi (rice cakes), bun with bean-jam filling, sweet rice jelly, bean jams, chunky sweet bean jelly, soft chunky sweet bean jelly, Kingyoku (literally, brocade balls), jelly, Kasutera sponge cake, and candy; various Western confectioneries such as bread, biscuit, cracker, cookie, pie, purine, buttercream, custard cream, shoe cream, waffle, sponge cake, donut, chocolate, chewing gum, caramel, nougat, and candy; ices such as ice cream and sherbet; syrups such as fruits preserved in syrup, and syrup for shaved ice; pastes such as flower paste, peanut paste, and fruit paste; processed foods of fruits and vegetables, such as jam, marmalade, food preserved in syrup, and candied fruit; Japanese pickles such as sliced vegetables pickled in soy sauce, pickled daikon (Japanese radish), and pickles of sliced turnip; seasonings for Japanese pickles, such as seasoning for pickled daikon (Japanese radish), and seasoning for Chinese cabbage pickles; meat products such as ham and sausage; fish meet products such as fish meat ham, fish meat sausage, boiled fish paste, tube-shaped fish paste cake, and deep-fried fish ball; various delicacies such as salted fish entrails of sea urchin and squid, vinegared kelp, dried seasoned tore squid, and mashed and seasoned fish of codfish, sea bream and shrimp; deli foods such as Tsukudani preserved food in soy sauce made from laver, edible wild plants, dried squid, small fish, and shellfish, cooked beans, fish boiled in broth, potato salad, and kobu maki (kelp roll); instant foods such as dairy products, fish meet, bottled products of meat, fruits and vegetables, canned products, pudding mix, pancake mix, instant juice, instant coffee, instant azuki-bean soup with rice cake, and instant soup; frozen foods; fruit and vegetable beverages, such as a beverage containing fruit juice, fruit juice, and vegetable juice; carbonated beverages such as cider and ginger ale; isotonic sport beverage coffee beverages such as isotonic beverage and amino acid beverage; tea-based beverages such as green tea; milk-based beverages such as lactic acid beverage and cocoa; alcoholic beverages such as Japanese spirit with soda, refined sake, and fruit liquor; energy drink; and baby food, therapeutic food, liquid food, drinkable preparation, and peptide foods.

To the high intensity sweetener-containing food or beverage product of the present invention, in addition to a saccharide polycondensate produced by the production method of the present invention, or a reduced product or a saccharide polycondensate composition thereof, one or more kinds of other water-soluble dietary fibers may be added. Examples of the other water-soluble dietary fiber include indigestible dextrin, polydextrose, soybean-derived water-soluble dietary fiber, hydrolyzed guar gum, glucomannan, inulin, pectin, sodium alginate and the like.

The content of the saccharide polycondensate in a food or beverage product in the present invention is not specifically limited, and can be adjusted to 0.02 to 20% by weight, preferably 0.05 to 15% by weight, and more preferably 0.1 to 10% by weight, in terms of the solid content from the viewpoint of efficiently exerting the body imparting effect and the effect of improving bad taste derived from a high intensity sweetener.

The content of the high intensity sweetener in the present invention can be appropriately adjusted according to the intended food or beverage product.

In the present invention, a sweet component used in a food or beverage product may be entirely supplemented with a high intensity sweetener, or other sweet components such as sucrose may be used in an auxiliary manner.

Specific examples of other sweet components include sweet components, for example, liquid sugars such as sucrose, glucose, fructose, and high fructose corn syrup; saccharides such as starch syrup, reduced sugar syrup, powder candy, honey, and oligosaccharides such as an isomaltooligosaccharide (isomaltose, isomaltotriose, panose, etc.) and lactosucrose; arabinose, isotrehalose, isomaltitol, erythritol, oligo-N-acetylglucosamine, galactose, galactosylsucrose, galactosyllactose, xylitol, xylose, a xylooligosaccharide (xylotriose, xylobiose, etc.), glycerol, curculin, a gentio-oligosaccharide (gentiobiose, gentiotriose, gentiotetraose, etc.), stachyose, dulcin, sorbose, a theande-oligosaccharide, trehalose, nigeria berry extract, a nigero-oligosaccharide (nigerose, etc.), neotrehalose, Neohesperidin dihydrochalcone, reduced palatinose, palatinose, a fructooligosaccharide (kestose, nystose, etc.), fructose, maltitol, maltose, a maltooligosaccharide (maltotriose, maltotetraose, maltopentaose, maltohexaose, maltoheptaose, etc.), mannitol, miracle fruit extract, Siraitia grosvenorii extract, lactitol, lactose, raffinose, rhamnose, ribose, an isomerized liquid sugar, a reduced isomaltooligosaccharide, a reduced xylooligosaccharide, a reduced gentio-oligosaccharide, a reduced sugar syrup, an enzymatically modified licorice, an enzymatically modified stevia, an enzymatically hydrolyzed licorice, a sugar-bound starch syrup (coupling sugar), a soy oligosaccharide, and an invert sugar.

The food or beverage product of the present invention may be those which are sold at a normal temperature, sold in a hot vendor, or sold in chilled food distribution, and can be produced by a conventional method, except for allowing to contain a high intensity sweetener and a saccharide polycondensate. It is possible to optionally add, in addition to the above-mentioned components, an emulsifier, a pigment, a flavoring agent, a juice, a puree, a sour agent, a seasoning, an antioxidant, a preservative, an extract, a starch adhesive, a thickener, a pH adjustor, liquors, vitamins, and minerals.

Application to Beer-Flavored Beverage

Due to rising health concerns in recent days, a beer-based alcoholic beverage with low calorie is now the focus of attention. There are proposed, as a method for producing a beer flavored alcoholic beverage with low calorie, a method in which fermentation is carried out by reducing a raw saccharide, and a method in which the formed alcohol is removed. However, the obtained beer flavored alcoholic beverage lacks in body, flavor, and body sensation in both methods. With the change in consumers' taste, there has been required a beer flavored beverage with enhanced body, flavor, and body sensation. As one of solutions to these problems, there has been developed a beer flavored alcoholic beverage in which body, flavor and body sensation are improved by using a dietary fiber. It is known that body and body sensation are improved by adding, for example, polydextrose or indigestible dextrin, which is a sort of water-soluble dietary fibers, to a beer flavored beverage (see, for example, Japanese Patent Application Laid-Open Publication No. 8-9953, Japanese Patent Application Laid-Open Publication No. 8-249, and Japanese Patent Application Laid-Open Publication No. 10-215848). However, these water-soluble dietary fibers had a problem that masking of flavor of a beer flavored alcoholic beverage is carried out by the masking effect, and thus impairing original flavor of the beverage. Some dietary fibers had a problem that flavor of a beer flavored alcoholic beverage is impaired since off-flavors such as sourness and sweetness derived therefrom are imparted to the beverage.

It was confirmed that when a saccharide polycondensate produced by the production method of the present invention, and a reduced product and a saccharide polycondensate composition thereof is added to a beer flavored beverage, body and smoothness are imparted to a beverage, and also neither reduction in flavor due to masking nor imparting of off-flavor occurs (below-mentioned Examples C1 to C4). Namely, according to the present invention, there is provided a beer flavored alcoholic beverage, containing a saccharide polycondensate produced by the production method of the present invention, and a reduced product and a saccharide polycondensate composition thereof added therein.

The "beer flavored alcoholic beverage", to which a saccharide polycondensate produced by the production method of the present invention, and a reduced product and a saccharide polycondensate composition thereof are added, includes, in addition to beer, low-malt beer, and other effervescent brewages and other effervescent liqueurs called "third beer" or "new genrea (category)" under liquor tax law, a low alcohol beer flavored fermented malt beverage. The "beer flavored beverage" in the present invention includes, in addition to a beer flavored alcoholic beverage, a non-alcoholic beer flavored beverage.

The beer flavored alcoholic beverage of the present invention can be produced by a conventional method which is generally used in beer, low-malt beer, and other effervescent brewages and other effervescent liqueurs called "third beer" or "new genrea (category)", except that a saccharide polycondensate is added. Namely, malt is mixed with warm water, or malt is mixed with secondary materials such as saccharides, starch and protein using warm water, and then an enzyme such as amylase is added, followed by saccharification and further filtration to prepare a wort. To the obtained wort, hop is added, followed by boiling and further filtration to prepare an unfermented liquid, and then yeast is added and fermentation and aging are carried out by a conventional method, and thus a fermented liquid can be obtained. In addition to the above-mentioned materials, additives such as a pigment and a flavoring agent may be appropriately added.

Among beer flavored beverages of the present invention, a non-alcoholic beer flavored beverage can be produced by extracting an alcohol from the beer flavored alcoholic beverage thus produced in the above manner, or may produced by adding a saccharide polycondensate to a beer flavored beverage obtained without fermentation.

Since the saccharide polycondensate is scarcely assimilated with yeast because of its chemical structure, timing of addition of the saccharide polycondensate is not specifically limited, and the saccharide polycondensate may be added to a wort or an unfermented liquid, together with other secondary materials before preparation of the wort (preparation step), or may be added to a wort or an unfermented liquid, together with hop after preparation of the wort and before fermentation, or may be added to a fermented liquid during a fermentation step, or may be added to a fermented liquid after a fermentation step.

To the beer flavored alcoholic beverage of the present invention, in addition to a saccharide polycondensate produced by the production method of the present invention, or a reduced product or a saccharide polycondensate composition thereof, one or more kinds of other water-soluble dietary fibers may be added. Examples of other water-soluble dietary fibers include indigestible dextrin, polydextrose, soybean-derived water-soluble dietary fiber, hydrolyzed guar gum, glucomannan, inulin, pectin, sodium alginate and the like.

The content of a saccharide polycondensate to a beer flavored alcoholic beverage of the present invention is not specifically limited, and can be adjusted to 0.1 to 10% by weight, and preferably 0.3 to 5% by weight, from the viewpoint of efficiently exerting the body imparting effect.

Application to Feed

It was confirmed that when a saccharide polycondensate produced by the production method of the present invention, and a reduced product and a saccharide polycondensate composition thereof are added to a feed, a dietary fiber can be given without impairing quality of the feed (see below-mentioned Examples E1 to E3). Namely, according to the present invention, there is provided a dietary fiber-reinforced feed containing a saccharide polycondensate produced by the production method of the present invention, and a reduced product and a saccharide polycondensate composition thereof added therein.

The "feed" in the present invention may be any feed. Examples of the feed, to which a saccharide polycondensate, and a reduced product and a saccharide polycondensate composition thereof, produced by the production method of the present invention can be given, include dog food, cat food, pet food, livestock feed, poultry feed, fish feed and the like.

The content of a saccharide polycondensate in the feed in the present invention is not specifically limited, and can be adjusted to 0.01 to 99% by weight, preferably 0.01 to 50% by weight, and more preferably 0.1 to 30% by weight, in terms of the solid content from the viewpoint of effectively adding a dietary fiber to the feed.

To the feed of the present invention, one or more kinds of other water-soluble dietary fibers may be added, in addition to a saccharide polycondensate, or a reduced product or a saccharide polycondensate composition thereof, produced by the production method of the present invention. Examples of the other water-soluble dietary fiber include indigestible dextrin, polydextrose, soybean-derived water-soluble dietary fiber, hydrolyzed guar gum, glucomannan, inulin, pectin, sodium alginate and the like.

The feed of the present invention can be produced by a conventional method, except that the feed is allowed to contain a saccharide polycondensate, or a reduced product or a saccharide polycondensate composition thereof, produced by the production method of the present invention. It is possible to optionally added, to the feed of the present invention, a saccharide, a protein, an amino acid, fats and oils, an emulsifier, a pigment, a seasoning, an antioxidant, a preservative, an extract, a starch adhesive, a thickener, a pH adjustor, vitamins, minerals, an antibiotic and the like.

EXAMPLES

The present invention will be specifically described below by way of examples, but the present invention is not limited to these examples.

Various measuring methods and analytical methods shown in Examples were carried out as follows.

Measurement of Dietary Fiber Content

Dietary fiber content is measured by high-performance liquid chromatography (enzymatic-HPLC method) disclosed in Eishin No. 13 dated Apr. 26, 1999 (with respect to an analytical method of nutrients in Nutrition Labelling Standards). Specifically, the measurement was made as follows.

First, 1 g of a sample is accurately weighed and 50 ml of 0.08 mol/l phosphate buffer is added, thereby confirming that pH is 6.0±0.5. To this is added 0.1 ml of a thermostable α-amylase (Sigma Corporation: derived from EC3.2.1.1 *Bacillus licheniformis*) solution and the solution is poured into boiling water, and then the mixture is left to stand for 30 minutes while stirring every 5 minutes. After cooling, pH is adjusted to 7.5±0.1 by adding a sodium hydroxide solution (1.1→100). A protease (Sigma Corporation: derived from EC3.4.21.62 *Bacillus licheniformis*) solution (0.1 ml) is added and the reaction is carried out for 30 minutes while shaking in a water bath at 60±2° C. After cooling, pH is adjusted to 4.3±0.3 by adding 0.325 mol/l hydrochloric acid. An amyloglucosidase (Sigma Corporation: derived from EC3.2.13 *Aspergillus niger*) solution (0.1 ml) is added and the reaction is carried out for 30 minutes while shaking in a water bath at 60±2° C. Immediately after completion of the above enzymatic modification, heating is carried out for 10 minutes in a boiling water bath. After cooling, 5 ml of glycerin (10→100) is added as an internal standard substance and water is added to make 100 ml of an enzymatically modified liquid. The enzymatically modified liquid (50 ml) is passed through a column (glass tube measuring 20 mm×300 mm) filled with 50 ml of an ion-exchange resin (OH type:H type=1:1) at a liquid passing velocity of 50 ml/hour and then water is passed through the column to make 200 ml of the total amount of an effluent. The obtained solution is concentrated in a rotary evaporator and water is added to make 20 ml of the total amount. The solution is filtered through a membrane filter having a pore size of 0.45 μm to obtain a test liquid.

Next, 20 μl of the test liquid was subjected to liquid chromatography and peak area values of glycerin and a dietary fiber fraction of the test liquid were measured.

Analysis conditions of liquid chromatography were as follows.

Detector: Differential refractometer

Column: ULTRON PS-80N (measuring φ8.0×300 mm, Shimadzu JLC Ltd.), two columns being connected Column temperature: 80° C.

Mobile phase: Pure water

Flow rate: 0.5 ml/minute

The content of a dietary fiber component was calculated by the following equation:

Dietary fiber component content (%)=[peak area of dietary fiber component/peak area of glycerin]× $f1$×[weight (mg) of internal standard glycerin/weight (mg) of weighed sample]×100 where f1 is a sensitivity ratio (0.82) of a peak area of glycerin and glucose.

Measurement of Coloration Degree

Coloration degree of a sample was determined by measuring an absorbance at 420 nm ($OD_{420}$) using an aqueous 20% (w/w) solution of various samples.

Analysis of Whiteness

Regarding the measurement of whiteness of a sample, various samples were adjusted to Bx.50 and whiteness (WI value) was measured by a spectrophotometer SE-2000 manufactured by Nippon Denshoku Industries Co., Ltd. After standardization by white reflection standard according to SE-15723, calculation was carried out in terms of WI at the time of measurement of pure water being 100, using pure water as blank. As a result, whiteness of Raites (manufactured by Danisco Japan Ltd.) of Comparative Example was 81.7, and whiteness of Fibersol 2 (manufactured by Matsutani Chemical Industry Co., Ltd.) was 80.3.

Measurement of Molecular Weight

Each sample was dissolved in pure water so as to adjust to 1% (w/v), and 1% (w/v) activated carbon was added, followed by boiling and further filtration through a 0.45 μm membrane filter. The filtrate was subjected to a treatment with an ion-exchange resin MB4, and then filtered through a 0.45 μm membrane filter and analyzed.

Analysis conditions are as follows.

Column: Shodex OHpak SB-803 HQ+SB-802.5HQ (measuring φ8.0×300 mm, Showa Denko K.K.)

Temperature: 40° C.

Solvent: 200 mM potassium nitrate, 0.9 ml/minute

Pressure: 67 $kgf/cm^2$

Apparatus: MALLS: Dawn Heleos-II (Wyatt Technology, USA) (λ=658 nm),

Room temperature RI: Optilab rEX (Wyatt Technology), 25° C.

σn/σc: 0.145

Analysis software: Astra (v.5.3.4.14, Wyatt Technology)

Injection volume: Bx.1×100 μl

Methylation Analysis

Regarding a method for quantitative determination of glycosidic linkages, a sample was methylated by a modified method of the below-mentioned "Hakomori's methylation method" (S. Hakomori, J. Biochem., 55, 205 (1964)), followed by hydrolysis and further gas chromatography thereby quantitatively determining the glycosidic linkages composing the sample.

1) The methylated and dehydrated sample (5 mg) is placed in a test tube (measuring 15ψ×100 mm) with a screw cap and dissolved by addition of 0.5 ml of DMSO. To the solution is added 60 mg of NaOH and, after maintaining at room temperature for 1 hour, 0.3 ml of methyl iodide is added, followed by the reaction at 60° C. for 1 hour. The mixture is stirred and cooled in ice water, and then the reaction is terminated by adding 1 ml of water. The mixture is fully shaken with addition of 1 ml of chloroform. The upper layer (aqueous layer) is collected with a pipette and discarded. The remaining layer is similarly washed with addition of 1 ml of water. This procedure is repeated 5 times. Cotton is placed on the bottom of a Pasteur pipette and anhydrous sodium sulfate is filled in the pipette to form a 4 cm- to 5 cm-thick layer, and the solution is passed through the layer for dehydration and then washed with chloroform. Subsequently, the solution is concentrated to dryness in a rotary evaporator.

2) Hydrolysis: With the addition of 1 ml of 4M trifluoroacetic acid, the methylated product is hydrolyzed at 100° C. for 1 hour, and the hydrolyzate is concentrated to dryness at 60° C. in a rotary evaporator.

3) Reduction: The hydrolyzate is dissolved in 0.5 ml of water, and the solution is alkalified with addition of 3 drops of ammonia water, and then left to stand at room temperature for 2 hours or more after addition of 10 mg of sodium borohydride. AMBERLITE MB4 (ORGANO CORPORATION) is added to the mixture until the mixture ceases foaming thereby terminating the reaction. The mixture is then dried at room temperature and further dried at room temperature with addition of 2 ml of methanol so as to remove the boric acid formed. This procedure is repeated 5 times.

4) Acetylation: With the addition of 0.5 ml of acetic anhydride and 0.5 ml of pyridine, the reduced product is acetylated by heating at 100° C. for 4 hours. With the addition of 2 ml of toluene, the product is concentrated to dryness in a rotary evaporator.

5) Desalting: The acetylated product is dissolved in 1 ml of chloroform and the solution is shaken with addition of 1 ml of water, and the aqueous layer is discarded. After repeating this procedure 5 times, chloroform is evaporated off from the resulting layer in a rotary evaporator.

6) Dissolving: The desalted product is dissolved in 0.5 ml of chloroform and analyzed by subjecting to gas chromatography.

7) Conditions for gas chromatography

Column: TC-17 fused silica capillary column measuring 30 m×0.25 mm ID, 1.0 µm thick film Column temperature: 50° C. for 1 minute, elevation to temperature to 280° C. at a rate of 10° C./minute, followed by maintaining at the same temperature Temperature of sample vaporizing chamber: 300° C.

Detection temperature: 300° C.

Flow rate: 2.5 ml/minute, Helium

Detecting unit: Hydrogen flame ionization detector

8) Measurement of Amount of Reduced Saccharide

DE was measured in accordance with Modified Somogyi Method (Starch Saccharide-Related Industrial Analysis (Food Chemicals Newspaper, Inc.) (Published on Nov. 1, 1991), pp. 11-13).

Example A

Saccharide Polycondensate and Production Thereof

Example A1

Study (1) of Various Catalysts in Saccharide Polycondensation

Examination was carried out, whether or not activated carbon has catalytic activity of a saccharide polycondensation reaction, while comparing with a citric acid catalyst, a phosphoric acid catalyst, a hydrochloric acid catalyst, and a mineral catalyst.

Regarding a sample using activated carbon as a catalyst, 15 g of a hydrol (High Glu #9465, DE94, solid content 65%, manufactured by Nihon Shokuhin Kako Co., Ltd.) and 10% (per solid content) of activated carbon (Purified Shirasagi, manufactured by Japan EnviroChemicals, Ltd.) were mixed in a stainless steel vessel, and then the mixture was reacted in a hot air dryer for 1 hour (at 180° C.). In case where citric acid, phosphoric acid, hydrochloric acid, and activated clay are used as catalysts, the reaction was carried out in the same manner as mentioned above, except that 1.5% (per solid content) citric acid, 0.135% (per solid content) phosphoric acid, 0.005% (per solid content) hydrochloric acid, and 0.2% (per solid content) activated clay were respectively used in place of activated carbon.

Figure 2:
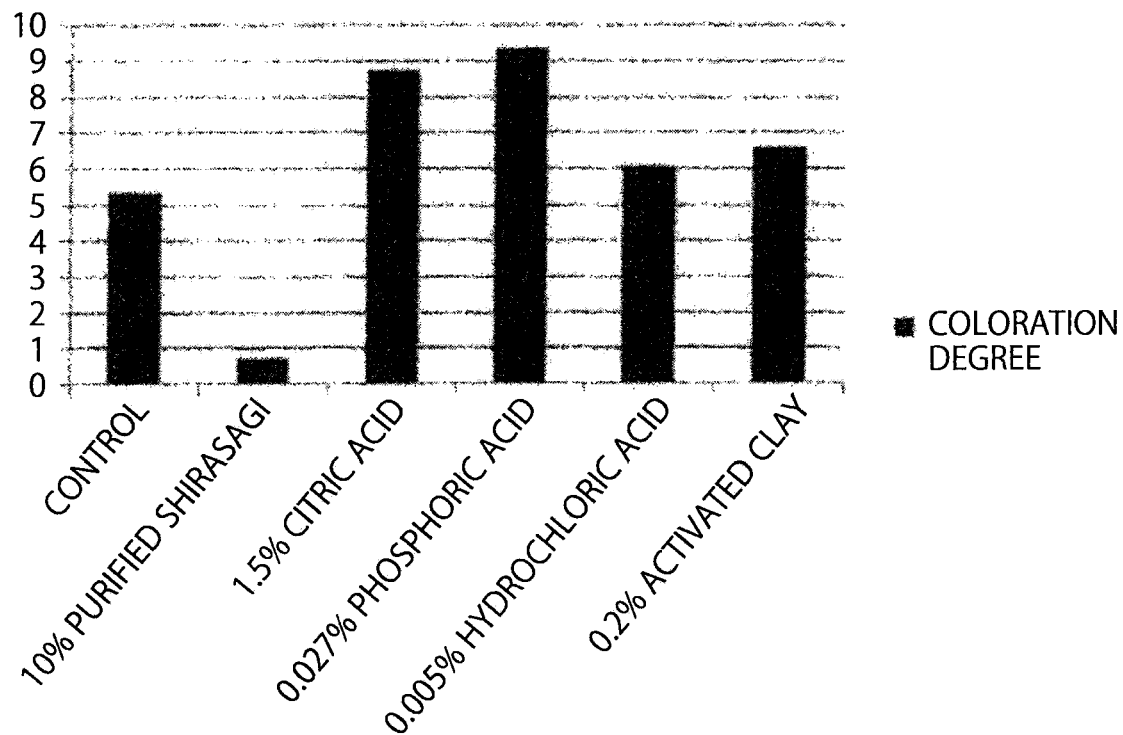
FIG. 2 is a diagram showing coloration degree of a saccharide polycondensate in case where activated carbon is used as a catalyst, and citric acid, phosphoric acid, hydrochloric acid, and activated clay are used as catalysts, in a saccharide polycondensation reaction.

With respect to the obtained samples, dietary fiber content and coloration degree were measured. The results are as shown in FIGS. 1 and 2. As is apparent from FIG. 1 and FIG. 2, any catalysts exhibited high dietary fiber content of 70% or more. Regarding the coloration degree, the reduction effect was recognized only when activated carbon is used. Namely, it has been found that the activated carbon has saccharide polycondensation catalytic activity which is almost the same as those of citric acid, phosphoric acid, hydrochloric acid, and activated clay, and also has the effect capable of remarkably decreasing the coloration degree of the saccharide polycondensate.

It has also been found that the activated carbon effectively reacts with a hydrol produced in the production process of a crystalline glucose.

Example A2

Study (2) of Various Catalysts in Saccharide Polycondensation

Examination was carried out, whether or not activated carbon has catalytic activity of a saccharide polycondensation reaction, even when using a polycondensation substrate other than glucose while comparing with a citric acid catalyst, a phosphoric acid catalyst, a hydrochloric acid catalyst, and a mineral catalyst.

Regarding a sample using activated carbon as a catalyst, 15 g of a saccharide polycondensate substrate solution (having a solid content of 66.7%) and 10% (per solid content) of activated carbon (Purified Shirasagi, manufactured by Japan EnviroChemicals, Ltd.) were mixed in a stainless steel vessel, and then the mixture was reacted in a hot air dryer for 1 hour (at 180° C.). In case where citric acid, phosphoric acid, hydrochloric acid, and activated clay are used as catalysts, the reaction was carried out in the same manner as mentioned above, except that 0.005% (per solid content) hydrochloric acid, 0.027% (per solid content) phosphoric acid, 1.5% (per solid content) citric acid, and 0.2% (per solid content) activated clay were respectively used in place of activated carbon.

The followings were used as a saccharide polycondensate substrate.

Test plot 1: Glucose and Dextrin (glucose:dextrin=70:30)

Test plot 2: Glucose and Oligosaccharide (glucose:oligosaccharide=70:30)

Test plot 3: Glucose and Sugar alcohol (glucose:sugar alcohol=90:10)

Test plot 4: Glucose and Galactose (glucose:galactose=50:50)

Test plot 5: Glucose and Xylose (glucose:xylose=50:50)

Test plot 6: Mannose

Test plot 7: Xylose

Anhydrous crystalline glucose "Medicalose" (manufactured by Nihon Shokuhin Kako Co., Ltd.) was used as glucose, "Pinedex #1" (manufactured by Matsutani Chemical Industry Co., Ltd.) was used as dextrin, "Branch-oligo" (manufactured by Nihon Shokuhin Kako Co., Ltd.) was used as oligosaccharide, and sorbitol (manufactured by TOWAKAGAKU corporation) was used as sugar alcohol, respectively. Also, galactose (manufactured by Nacalai Tesque, Inc.), xylose (Cica First Grade, manufactured by KANTO CHEMICAL CO., INC.), and mannose (Wako Special Grade, manufactured by Wako Pure Chemical Industries, Ltd.) were used.

Regarding the obtained samples, dietary fiber content and coloration degree were measured. The results are as shown in Table 1 and Table 2.

TABLE 1

Dietary fiber content (%)

| | Test plot 1 | Test plot 2 | Test plot 3 | Test plot 4 | Test plot 5 | Test plot 6 | Test plot 7 |
|---|---|---|---|---|---|---|---|
| No catalyst | 59 | 67 | 67 | 78 | 89 | 85 | 86 |
| 10% Activated carbon | 83 | 83 | 81 | 90 | 94 | 94 | 93 |
| 0.005% Hydrochloric acid | 84 | 83 | 82 | 92 | 93 | 92 | 89 |
| 0.027% Phosphoric acid | 86 | 86 | 83 | 91 | 94 | 92 | 90 |
| 1.5% Citric acid | 84 | 85 | 83 | 91 | 94 | 91 | 91 |
| 0.2% Activated clay | 83 | 85 | 81 | 90 | 92 | 92 | 91 |

TABLE 2

Coloration degree (aqueous 20% solution, $OD_{420}$)

| | Test plot 1 | Test plot 2 | Test plot 3 | Test plot 4 | Test plot 5 | Test plot 6 | Test plot 7 |
|---|---|---|---|---|---|---|---|
| No catalyst | 7.3 | 12.8 | 3.7 | 7.4 | 8.5 | 6.4 | 83 |
| 10% Activated carbon | 0.8 | 0.6 | 0.2 | 1.8 | 0.8 | 3.6 | 1.4 |
| 0.005% Hydrochloric acid | 25.2 | 29.0 | 13.2 | 26.2 | 20.6 | 21.2 | 19.1 |
| 0.027% Phosphoric acid | 3.2 | 3.5 | 1.7 | 5.4 | 6.9 | 11.7 | 5.8 |
| 1.5% Citric acid | 4.1 | 5.1 | 1.6 | 6.0 | 5.7 | 11.7 | 6.1 |
| 0.2% Activated clay | 8.8 | 5.3 | 3.3 | 5.4 | 4.0 | 9.7 | 11.2 |

As is apparent from Table 1 and Table 2, any catalysts exhibited high dietary fiber content of 70% or more even when using a polycondensation substrate other than glucose. Regarding the coloration degree, the reduction effect was recognized only when activated carbon is used. Namely, it has been found that even when a saccharide polycondensate substrate other than glucose is used, the activated carbon has saccharide polycondensation catalytic activity which is almost the same as those of hydrochloric acid, citric acid, and activated clay, and also has the effect capable of remarkably decreasing the coloration degree of the saccharide polycondensate.

Example A3

Study (1) of Reaction Conditions of Activated Carbon Catalyst

In a saccharide polycondensation reaction using an activated carbon catalyst, an influence of the reaction temperature and reaction time exerted on the dietary fiber content and coloration degree of a reaction product was examined.

Regarding a sample using a hydrol as a substrate, 15 g of a hydrol (High Glu #9465, manufactured by Nihon Shokuhin Kako Co., Ltd.) and 1 g of activated carbon (Purified Shirasagi, manufactured by Japan EnviroChemicals, Ltd.) were mixed in a stainless steel vessel, and then the sample was placed in a hot air dryer at 100° C. or lower and reacted under various temperature conditions for 1 minute to 3 hours, using an operating program (elevation of a temperature at about 2.5° C./minute, cooling at about 3.3° C./minute), after reaching a predetermined temperature. After the reaction, the reaction product was dissolved in 50 ml of pure water and the solution was suction-filtered through a 5.0 μm filter to obtain various samples for analysis. A sample using glucose as a substrate was reacted in the same manner as mentioned above, using 10 g of an anhydrous crystalline glucose (Medicalose, manufactured by Nihon Shokuhin Kako Co., Ltd.) and 1 g of Purified Shirasagi.

Figure 3:
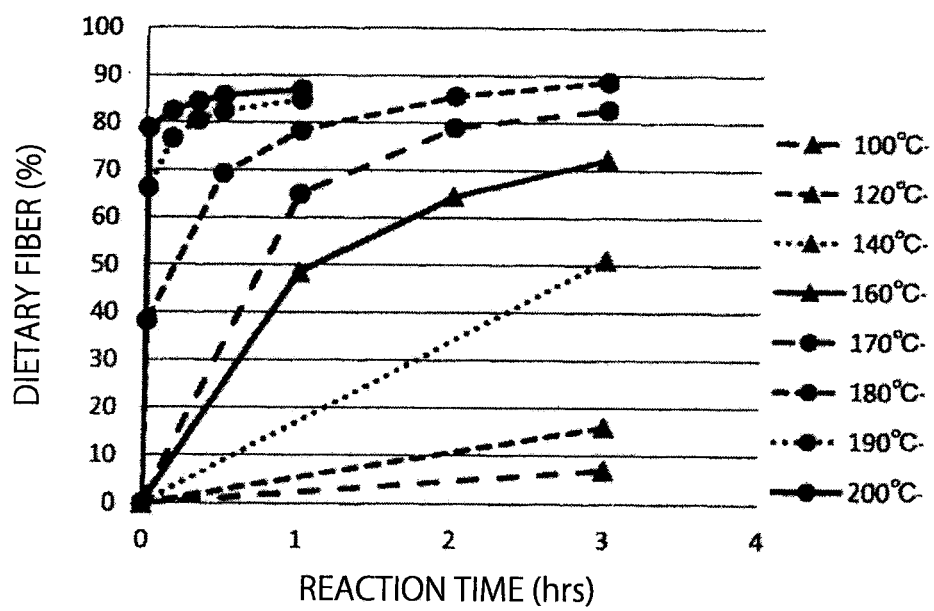
FIG. 3 is a diagram showing a change in content of a dietary fiber in a saccharide polycondensate over time at each reaction temperature, in a saccharide polycondensation reaction in which a hydrol is used as a reaction substrate and activated carbon is used as a catalyst.
Figure 4:
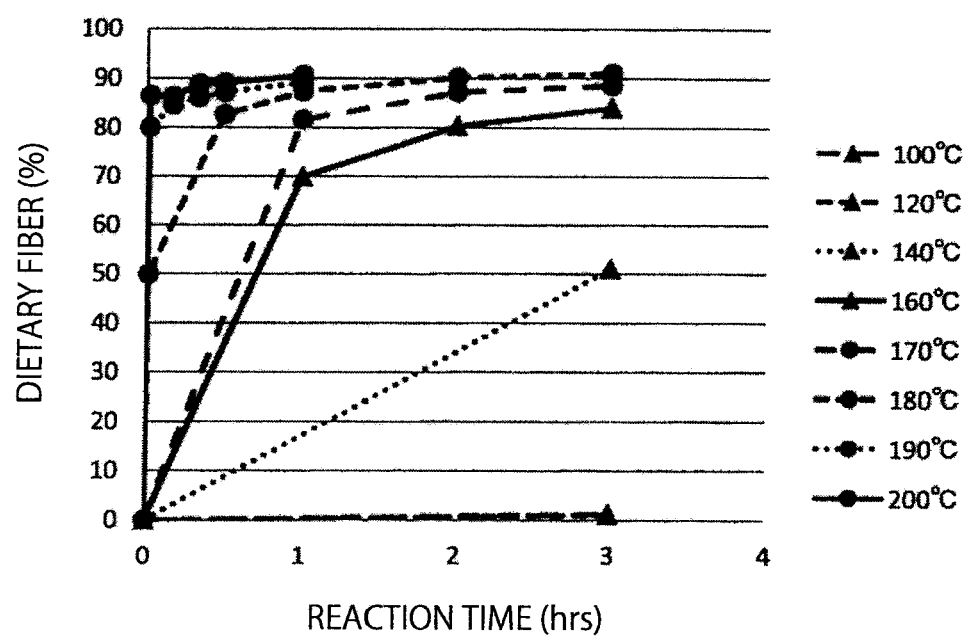
FIG. 4 is a diagram showing a change in content of a dietary fiber in a saccharide polycondensate over time at each reaction temperature, in a saccharide polycondensation reaction in which an anhydrous crystalline glucose is used as a reaction substrate and activated carbon is used as a catalyst.
Figure 5:
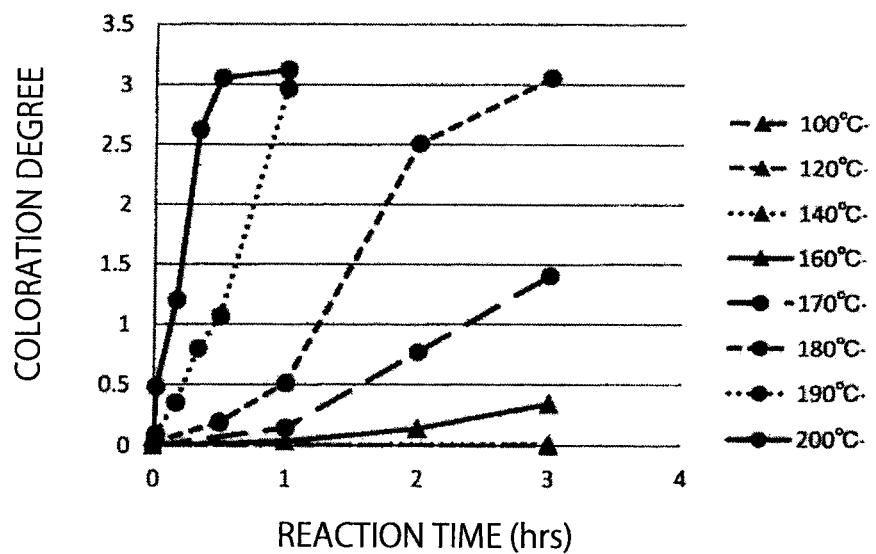
FIG. 5 is a diagram showing a change in coloration degree over time of a saccharide polycondensate at each reaction temperature, in a saccharide polycondensation reaction in which a hydrol is used as a reaction substrate and activated carbon is used as a catalyst.
Figure 6:
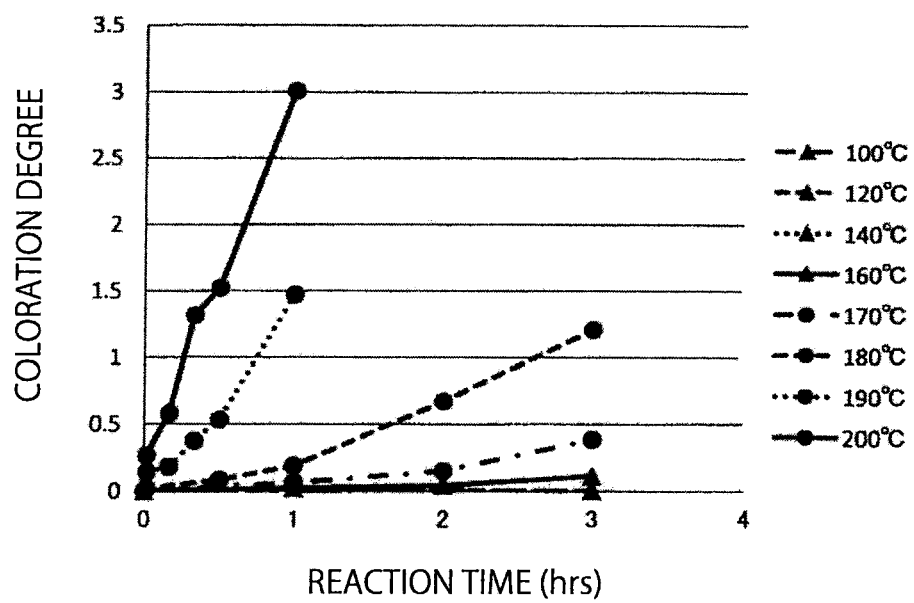
FIG. 6 is a diagram showing a change in coloration degree over time of a saccharide polycondensate at each reaction temperature, in a saccharide polycondensation reaction in which an anhydrous crystalline glucose is used as a reaction substrate and activated carbon is used as a catalyst.

The results of the analysis of the dietary fiber content every elapsed time under each temperature condition are as shown in FIG. 3 and FIG. 4. The results of measurement of the coloration degree of a 20% (w/w) solution every elapsed time under each temperature condition are as shown in FIG. 5 and FIG. 6.

As is apparent from FIGS. 3 to 6, the dietary fiber content of 75% or more is obtained within a short time as the reaction temperature elevates, and also intense coloration occurs as the reaction temperature elevates. The reaction condition, under which the dietary fiber content of 75% or more and low coloration degree ($OD_{420}$ of 2.0 or less at Bx.20) are attained by reacting the hydrol, was 1 hour (78.4%) at 180° C., 10 minutes (76.6%) at 190° C., and 1 minute (78.9%) at 200° C. The reaction condition, under which the dietary fiber content of 75% or more and low coloration degree ($OD_{420}$ of 2.0 or less at Bx.20) are attained by reacting the hydrol, was 30 minutes (82.7%) at 180° C., 1 minute (80.4%) at 190° C., and 1 minute (86.5%) at 200° C.

Example A4

Study (2) of Reaction Conditions of Activated Carbon Catalyst

In a saccharide polycondensation reaction using an activated carbon catalyst, an influence of the reaction under vacuum condition exerted on the dietary fiber content and coloration degree of a reaction product was examined.

Regarding a sample in which activated carbon is used as a catalyst, and an anhydrous crystalline glucose (Table 3 and Table 4, test plot A) or a hydrol (Table 3 and Table 4, test plot B) is used as a substrate, 10 g of an anhydrous crystalline glucose (Medicalose composition: DE100, manufactured by Nihon Shokuhin Kako Co., Ltd.) or a hydrol (High Glu #9465, manufactured by Nihon Shokuhin Kako Co., Ltd.) solid component was mixed with 1 g of Purified Shirasagi (manufactured by Japan EnviroChemicals, Ltd.) in a stainless steel vessel. The vessel was covered with an aluminum foil and a hole was appropriately opened, and then the mixture was quickly placed in a vacuum dryer maintained at 200° C. After reaching 200° C., the temperature was maintained at 200° C. for 1 hour. After the reaction for 1 hour, the reaction product was quickly taken out and then cooled at room temperature. The reaction in the vacuum dryer was carried out with evacuation (100 mmHg) or without evacuation. In the case of evacuating, evacuation was initiated after the sample was warmed in advance and placed in the vacuum dryer.

The results of the measurement of the coloration degree of the reaction product under vacuum and non-vacuum conditions are as shown in Table 3. The results of analysis of the dietary fiber content of the reaction product under vacuum and non-vacuum conditions are as shown in Table 4.

TABLE 3

Coloration degree ($OD_{420}$ of aqueous 20% solution)

| | Test plot A | Test plot B |
|---|---|---|
| Without vacuum | 2.3832 | 2.0304 |
| With vacuum | 0.5736 | 0.8478 |

TABLE 4

Dietary fiber content (%)

| | Test plot A | Test plot B |
|---|---|---|
| Without vacuum | 85.0 | 86.3 |
| With vacuum | 84.4 | 89.0 |

As shown in Table 3, when the anhydrous crystalline glucose is used in the polycondensation reaction, the coloration degree drastically decreased in the case of the reaction with vacuum as compared with the case of the reaction without vacuum. Similarly, even when the hydrol is used in the polycondensation reaction, a saccharide polycondensate with very low coloration degree was obtained by evacuation.

Example A5

Study (1) of Saccharide Substrate

In a saccharide polycondensation reaction using an activated carbon catalyst, the reaction was carried out by allowing glucose to coexist with oligosaccharide and dextrin, and properties of a reaction product were examined.

Regarding a saccharide polycondensate sample using glucose together with oligosaccharide, an anhydrous crystalline glucose (Medicalose, manufactured by Nihon Shokuhin Kako Co., Ltd.) (used as a Bx.65 solution), various oligosaccharides, and 1 g of Purified Shirasagi (manufactured by Japan EnviroChemicals, Ltd.) were placed in a stainless steel vessel and mixed, and then the mixture was reacted at 180° C. for 1 hour using a hot air dryer after reaching to a predetermined temperature. The addition amounts of crystalline glucose and various oligosaccharides were set to 10 g in total in terms of the solid content, and a solid content ratio of crystalline glucose and various oligosaccharides was set to 10% each. Fuji-oligo G67 (composition: DE26, manufactured by Nihon Shokuhin Kako Co., Ltd.), MC-55 (composition: DE47, manufactured by Nihon Shokuhin Kako Co., Ltd.), and Branch-oligo (composition: DE23, manufactured by Nihon Shokuhin Kako Co., Ltd.) were used as oligosaccharides.

After the reaction, the reaction product was dissolved in 50 ml of pure water and the solution was suction-filtered through a 5.0 μm filter to obtain various samples for analysis.

Regarding a saccharide polycondensate sample in which glucose is allowed to coexist with dextrin, an anhydrous crystalline glucose (Medicalose, manufactured by Nihon Shokuhin Kako Co., Ltd.) (used as a Bx.65 solution), various aqueous 50% (W/W) dextrin solutions, and 1 g of Purified Shirasagi (manufactured by Japan EnviroChemicals, Ltd.) were placed in a stainless steel vessel and mixed, and then the mixture was reacted for 1 hour using a hot air dryer after reaching 180° C. The addition amounts of anhydrous crystalline glucose and various dextrins were set to 10 g in total in terms of the solid content, and a solid content ratio of anhydrous crystalline glucose and various dextrins was set to 10% each. Pinedex #1 (composition: DE8, manufactured by Matsutani Chemical Industry Co., Ltd.), Pinedex #2 (composition: DE11, manufactured by Matsutani Chemical Industry Co., Ltd.), Pinedex #3 (composition: DE25, manufactured by Matsutani Chemical Industry Co., Ltd.), Pinedex #100 (composition: DE4, manufactured by Matsutani Chemical Industry Co., Ltd.), and clusterdextrin (composition: DE3, manufactured by Nihon Shokuhin Kako Co., Ltd.) (all of which are used as a Bx.65 solution) were used as dextrins. After the reaction, the reaction product was dissolved in 50 ml of pure water and the solution was suction-filtered through a 5.0 μm filter to obtain various samples for analysis.

Regarding the obtained saccharide polycondensates, dietary fiber content and coloration degree were measured. The results are as shown in Tables 5 to 8.

TABLE 5

Dietary fiber content (%)

| Blend ratio (Glc:Origosaccharide) | MC-55 | Fuji-oligo G67 | Branch-oligo |
|---|---|---|---|
| Glc:Oligosaccharide = 0:100 | 77 | 58 | 58 |
| Glc:Oligosaccharide = 10:90 | 77 | 69 | 68 |
| Glc:Oligosaccharide = 20:80 | 79 | 72 | 71 |
| Glc:Oligosaccharide = 30:70 | 79 | 75 | 74 |
| Glc:Oligosaccharide = 40:60 | 79 | 79 | 79 |
| Glc:Oligosaccharide = 50:50 | 79 | 80 | 78 |
| Glc:Oligosaccharide = 60:40 | 80 | 81 | 81 |
| Glc:Oligosaccharide = 70:30 | 81 | 82 | 82 |
| Glc:Oligosaccharide = 80:20 | 82 | 83 | 81 |
| Glc:Oligosaccharide = 90:10 | 84 | 84 | 84 |
| Glc:Oligosaccharide = 100:0 | 83 | 83 | 83 |

Glc: anhydrous crystalline glucose

TABLE 6

Coloration degree ($OD_{420}$ of aqueous 20% solution)

| Blend ratio (Glc:Origosaccharide) | MC-55 | Fuji-oligo G67 | Branch-oligo |
|---|---|---|---|
| Glc:Oligosaccharide = 0:100 | 0.35 | 0.12 | 0.08 |
| Glc:Oligosaccharide = 10:90 | 0.35 | 0.22 | 0.14 |
| Glc:Oligosaccharide = 20:80 | 0.42 | 0.35 | 0.20 |
| Glc:Oligosaccharide = 30:70 | 0.55 | 0.45 | 0.32 |
| Glc:Oligosaccharide = 40:60 | 0.52 | 0.59 | 0.50 |
| Glc:Oligosaccharide = 50:50 | 0.61 | 0.71 | 0.64 |
| Glc:Oligosaccharide = 60:40 | 0.61 | 0.80 | 0.53 |
| Glc:Oligosaccharide = 70:30 | 0.60 | 0.99 | 0.74 |
| Glc:Oligosaccharide = 80:20 | 0.97 | 1.04 | 0.66 |
| Glc:Oligosaccharide = 90:10 | 0.90 | 0.95 | 0.89 |
| Glc:Oligosaccharide = 100:0 | 0.84 | 0.84 | 0.84 |

Glc: anhydrous crystalline glucose

TABLE 7

Dietary fiber content (%)

| Blend ratio (Glc:Dextrin) | Pinedex #1 | Pinedex #2 | Pinedex #3 | Pinedex #100 | Cluster Dextrin |
|---|---|---|---|---|---|
| Glc:Dextrin = 100:0 | 82 | 82 | 82 | 82 | 82 |
| Glc:Dextrin = 70:30 | 76 | 77 | 77 | 79 | 80 |
| Glc:Dextrin = 50:50 | 74 | 74 | 77 | 78 | 77 |
| Glc:Dextrin = 30:70 | 72 | 71 | 75 | 68 | 73 |
| Glc:Dextrin = 0:100 | 15 | 15 | 66 | 20 | 39 |

Glc: anhydrous crystalline glucose

TABLE 8

| Coloration degree (OD$_{420}$ of aqueous 20% solution) | | | | | |
|---|---|---|---|---|---|
| Blend ratio (Glc:Dextrin) | Pinedex #1 | Pinedex #2 | Pinedex #3 | Pinedex #100 | Cluster Dextrin |
| Glc:Dextrin = 100:0 | 0.66 | 0.66 | 0.66 | 0.66 | 0.66 |
| Glc:Dextrin = 70:30 | 0.86 | 0.93 | 0.63 | 0.95 | 0.98 |
| Glc:Dextrin = 50:50 | 0.66 | 0.65 | 0.58 | 0.79 | 0.58 |
| Glc:Dextrin = 30:70 | 0.57 | 0.46 | 0.54 | 0.45 | 0.60 |
| Glc:Dextrin = 0:100 | 0.04 | 0.04 | 0.20 | 0.12 | 0.18 |

Glc: anhydrous crystalline glucose

As shown in Tables 5 to 8, it has been found that the saccharide polycondensation reaction proceeds in the presence of activated carbon even when glucose is allowed to coexist with oligosaccharide and dextrin, and thus making it possible to produce a saccharide polycondensate which is water-soluble and contains an enriched dietary fiber.

Example A6

Study (2) of Saccharide Substrate

In a saccharide polycondensation reaction using an activated carbon catalyst, the reaction was carried out in case where only saccharide other than glucose is used as a polycondensation substrate, and properties of a reaction product were examined. Also, in a saccharide polycondensation reaction using an activated carbon catalyst, the reaction was carried out by allowing saccharide to coexist with saccharide other than glucose, and properties of the reaction product were examined.

Regarding a saccharide polycondensate sample using only saccharide other than glucose as a polycondensation substrate, various saccharides each having a solid content of 1 g and 0.1 g of activated carbon (Purified Shirasagi, manufactured by Japan EnviroChemicals, Ltd.) were mixed in a stainless steel vessel, and then the sample was placed in a hot air dryer at 100° C. or lower and reacted for 30 minutes, using an operating program (elevation of a temperature at about 2.5° C./minute, cooling at about 3.3° C./minute), after reaching 180° C. Saccharides used in a test were as follows: an anhydrous crystalline glucose (Medicalose, manufactured by Nihon Shokuhin Kako Co., Ltd.), mannose (Wako Special Grade, manufactured by Wako Pure Chemical Industries, Ltd.), galactose (manufactured by Nacalai Tesque, Inc.), xylose (Cica First Grade, manufactured by KANTO CHEMICAL CO., INC.), arabinose (manufactured by Nakarai Chemicals Ltd.), ribose (manufactured by KANTO CHEMICAL CO., INC.), maltose (manufactured by Nihon Shokuhin Kako Co., Ltd.), lactose monohydrate (manufactured by KANTO CHEMICAL CO., INC.). After the reaction, the reaction product was dissolved in pure water and the solution was suction-filtered through a 0.45 μm filter to obtain various samples for analysis.

Regarding a heterosaccharide polycondensate sample, an anhydrous crystalline glucose (Medicalose, manufactured by Nihon Shokuhin Kako Co., Ltd.), monosaccharide other than glucose, namely, a saccharide having an entire solid content of 10 g prepared by mixing xylose (Cica First Grade, manufactured by KANTO CHEMICAL CO., INC.), galactose (manufactured by Nacalai Tesque, Inc.), and mannose (Wako Special Grade, manufactured by Wako Pure Chemical Industries, Ltd.) so as to set a solid content ratio to 0 to 100%, and 1.0 g of activated carbon (Purified Shirasagi, manufactured by Japan EnviroChemicals, Ltd.) were mixed in a stainless steel vessel, and then the sample was placed in a hot air dryer at 100° C. or lower and reacted for 30 minutes, using an operating program (elevation of a temperature at about 2.5° C./minute, cooling at about 3.3° C./minute), after reaching 180° C. After the reaction, the reaction product was dissolved so as to adjust to 20% (W/W), and the solution was suction-filtered through a 0.45 μm filter to obtain various samples for analysis.

The results of the measurement of the dietary fiber content and coloration degree of the heterosaccharide polycondensate in which various saccharides are polycondensed are as shown in Table 9.

TABLE 9

| Saccharide polycondensates derived from various saccharides | | |
|---|---|---|
| Raw materials | Dietary fiber (%) | Coloration degree (Bx. 20) |
| Glucose | 79.1 | 0.09 |
| Mannose | 91.1 | 1.24 |
| Galactose | 87.1 | 0.43 |
| Xylose | 92.6 | 0.18 |
| Arabinose | 96.9 | 0.46 |
| Ribose | 86.9 | 1.46 |
| Maltose | 74.7 | 0.11 |
| Lactose | 88.8 | 7.00 |

As is apparent from Table 9, it is possible to produce a saccharide polycondensate which has low coloration and high dietary fiber content, even when saccharide other than glucose is used as a polycondensation substrate.

The results of the measurement of the dietary fiber content and coloration degree of the heterosaccharide polycondensate prepared by using various monosaccharides and glucose in any mixing ratio are as shown in Tables 10 to 12.

TABLE 10

| Glucose (Glc) and Xylose (Xyl) | | |
|---|---|---|
| Samples | Dietary fiber (%) | Coloration degree (Bx. 20) |
| Glc:Xyl = 0:100 | 92.6 | 0.23 |
| Glc:Xyl = 10:90 | 92.7 | 0.32 |
| Glc:Xyl = 20:80 | 95.6 | 0.31 |
| Glc:Xyl = 30:70 | 95.0 | 0.32 |
| Glc:Xyl = 40:60 | 94.5 | 0.23 |
| Glc:Xyl = 50:50 | 93.0 | 0.21 |
| Glc:Xyl = 60:40 | 87.4 | 0.25 |
| Glc:Xyl = 70:30 | 87.7 | 0.23 |
| Glc:Xyl = 80:20 | 86.6 | 0.20 |
| Glc:Xyl = 90:10 | 86.0 | 0.23 |
| Glc:Xyl = 100:0 | 84.0 | 0.15 |

TABLE 11

| Glucose (Glc) and Xylose (Gal) | | |
|---|---|---|
| Samples | Dietary fiber (%) | Coloration degree (Bx. 20) |
| Glc:Gal = 0:100 | 94.9 | 0.43 |
| Glc:Gal = 10:90 | 94.1 | 0.38 |
| Glc:Gal = 20:80 | 92.2 | 0.29 |
| Glc:Gal = 30:70 | 91.5 | 0.26 |
| Glc:Gal = 40:60 | 90.8 | 0.25 |
| Glc:Gal = 50:50 | 90.2 | 0.30 |
| Glc:Gal = 60:40 | 89.2 | 0.23 |
| Glc:Gal = 70:30 | 87.8 | 0.19 |
| Glc:Gal = 80:20 | 86.9 | 0.15 |

TABLE 11-continued

Glucose (Glc) and Xylose (Gal)

| Samples | Dietary fiber (%) | Coloration degree (Bx. 20) |
|---|---|---|
| Glc:Gal = 90:10 | 84.9 | 0.13 |
| Glc:Gal = 100:0 | 84.0 | 0.13 |

TABLE 12

Glucose (Glc) and Mannose (Man)

| Samples | Dietary fiber (%) | Coloration degree (Bx. 20) |
|---|---|---|
| Glc:Man = 0:100 | 91.1 | 1.24 |
| Glc:Man = 10:90 | 88.7 | 0.86 |
| Glc:Man = 20:80 | 88.8 | 0.57 |
| Glc:Man = 30:70 | 88.8 | 0.66 |
| Glc:Man = 40:60 | 87.8 | 0.45 |
| Glc:Man = 50:50 | 87.5 | 0.41 |
| Glc:Man = 60:40 | 86.9 | 0.27 |
| Glc:Man = 70:30 | 84.9 | 0.22 |
| Glc:Man = 80:20 | 84.4 | 0.14 |
| Glc:Man = 90:10 | 82.6 | 0.10 |
| Glc:Man = 100:0 | 83.1 | 0.09 |

As shown in Tables 10 to 12, the saccharide polycondensate using, in addition to glucose, galactose and mannose as polycondensation raw materials exhibited an increase in dietary fiber content as the ratios of these monosaccharides increase, as compared with the saccharide polycondensate using glucose alone. There was a tendency that the coloration degree slightly increases as the ratio of mannose increases in the saccharide polycondensate using mannose. In contrast, in the saccharide polycondensate using xylose and galactose, the coloration degree kept constant even when the ratios of these saccharides increase.

It has been found that the saccharide polycondensate obtained by allowing glucose to coexist with monosaccharide other than glucose enables preparation of a saccharide polycondensate having high dietary fiber content by using arabinose, xylose, mannose and galactose in combination with glucose in any ratio. Namely, it has been shown that it is possible to produce a saccharide polycondensate with the composition closer to that of a plant-derived dietary fiber by using monosaccharide other than glucose as a polycondensation raw material in the present invention. It has also been found that it is possible to produce a saccharide polycondensate, which has low coloration and high dietary fiber content, even when the polycondensation reaction is carried out using only monosaccharide other than glucose. Namely, it was shown that the production method of the present invention is effective to not only the polycondensation reaction of glucose, but also the polycondensation reaction of monosaccharide other than glucose.

Example A7

Study (3) of Saccharide Substrate

In a saccharide polycondensation reaction using an activated carbon catalyst, the reaction was carried out by allowing glucose to coexist with various sugar alcohols, and properties of the reaction product were examined.

Regarding a saccharide polycondensate sample, an anhydrous crystalline glucose having a solid content of 9.0 g (Medicalose, manufactured by Nihon Shokuhin Kako Co., Ltd.) and various sugar alcohols each having a solid content of 1.0 g were mixed with 1.0 g of activated carbon (Purified Shirasagi, manufactured by Japan EnviroChemicals, Ltd.) in a stainless steel vessel, and then the sample was placed in a hot air dryer at 100° C. or lower and reacted for 30 minutes, using an operating program (elevation of a temperature at about 2.5° C./minute, cooling at about 3.3° C./minute), after reaching 180° C. Sugar alcohols used in a test were as follows: anhydrous crystalline glucose (Medicalose, manufactured by Nihon Shokuhin Kako Co., Ltd.) (for comparison), sorbitol (manufactured by TOWAKAGAKU corporation), galactitol (manufactured by Tokyo Chemical Industry Co., Ltd.), mannitol (Wako Special Grade, manufactured by Wako Pure Chemical Industries, Ltd.), xylitol (manufactured by TOWAKAGAKU corporation), erythritol (Wako Special Grade, manufactured by Wako Pure Chemical Industries, Ltd.), lactitol (manufactured by Funakoshi Corporation), maltitol (manufactured by Funakoshi Corporation), inositol (manufactured by KANTO CHEMICAL CO., INC.), and glycerol (manufactured by KANTO CHEMICAL CO., INC.). After the reaction, the reaction product was dissolved in 5 ml of pure water and the solution was suction-filtered through a 0.45 μm filter to obtain various samples for analysis.

The results of the measurement of the dietary fiber content and coloration degree of the saccharide polycondensate in which glucose and various sugar alcohols are polycondensed are as shown in Table 13.

TABLE 13

Glucose and various sugar alcohols

| | Dietary fiber (%) | Coloration degree (Bx. 20) |
|---|---|---|
| Glucose | 79.1 | 0.09 |
| Sorbitol | 79.2 | 0.07 |
| Galactitol | 78.8 | 0.06 |
| Mannitol | 76.7 | 0.08 |
| Xytol | 77.6 | 0.07 |
| Erythritol | 75.4 | 0.06 |
| Lactitol | 82.3 | 0.08 |
| Multitol | 81.5 | 0.09 |
| Inocitol | 73.5 | 0.10 |
| glycerol | 74.9 | 0.06 |

As shown in Table 13, it has been found that it is possible to produce a saccharide polycondensate, which has low coloration and high dietary fiber content, even when glucose and sugar alcohol are used as polycondensation substrates. Namely, it was shown that sugar alcohol can also be used as a polycondensation raw material in the production method of the present invention.

Example A8

Production (1) of Saccharide Polycondensate

To 400 g of an anhydrous crystalline glucose (Medicalose, manufactured by Nihon Shokuhin Kako Co., Ltd.), 10% (per solid content) of activated carbon (Purified Shirasagi, manufactured by Japan EnviroChemicals, Ltd.) was added and, after mixing, the mixture was placed in a heating reactor and heated at 180° C. for 30 minutes to obtain a sample. After cooling to room temperature, an aqueous 20% solution prepared from this sample was filtered to completely remove the activated carbon, and thus a soluble saccharide was obtained. The obtained soluble saccharide fraction was subjected to decolorization filtration with activated carbon, decolorization with an ion-exchange resin, and further evaporator concentration, and then dried. As a result, about 330 g of a product was obtained and the product had a dietary fiber content of 79.1%, a coloration degree of 0.13 (Bx.50), a whiteness of 98.5 (Bx.50), and an average molecular weight of 3,300.

The saccharide polycondensate produced in Example A8 was partially reacted at room temperature for 3 hours, using sodium cyanoborohydride, and the obtained sample had DE 0.

The saccharide polycondensate produced in Example A8 was partially subjected to resin fractionation using TOYO-PEARL HW-40S (measuring φ5.0×90 cm) as a carrier. As a result, the product obtained by removing a low molecular component of di- or lower saccharides had a dietary fiber content of 94.7%, and the product obtained by treating with α-amylase and glucoamylase, followed by resin fractionation had a dietary fiber content of 99.0%.

Example A9

Production (2) of Saccharide Polycondensate

To 400 g of a solid component of hydrol (High Glu #9465, manufactured by Nihon Shokuhin Kako Co., Ltd.), 10% (per solid content) of activated carbon (Purified Shirasagi, manufactured by Japan EnviroChemicals, Ltd.) was added and, after mixing, the mixture was placed in a heating reactor and heated at 180° C. for 60 minutes to obtain a sample. After cooling to room temperature, an aqueous 20% solution prepared from this sample was filtered to completely remove the activated carbon, and thus a soluble saccharide was obtained. The obtained soluble saccharide fraction was subjected to decolorization filtration with activated carbon, decolorization with an ion-exchange resin, and further evaporator concentration, and then dried. As a result, about 300 g of a product was obtained and the product had a dietary fiber content of 76.8%, a coloration degree of 0.76 (Bx.50), a whiteness of 83.0 (Bx.50), and an average molecular weight of 3,300.

The saccharide polycondensate produced in Example A9 was partially reacted at room temperature for 3 hours, using sodium cyanoborohydride, and the obtained sample had DE 0.3.

The saccharide polycondensate produced in Example A9 was partially subjected to resin fractionation using TOYO-PEARL HW-40S (measuring φ5.0×90 cm) as a carrier. As a result, the product obtained by removing a low molecular component of di- or lower saccharides had a dietary fiber content of 93.3%, and the product obtained by treating with α-amylase and glucoamylase, followed by resin fractionation had a dietary fiber content of 99.0%.

Example A10

Production (3) of Saccharide Polycondensate

To an aqueous Bx.65 solution prepared by mixing 120 g of a solid component of oligosaccharide syrup (Branch-oligo, manufactured by Nihon Shokuhin Kako Co., Ltd.) with 280 g of a solid component of an anhydrous crystalline glucose (Medicalose, manufactured by Nihon Shokuhin Kako Co., Ltd.), 10% (per solid content) of activated carbon (Purified Shirasagi, manufactured by Japan EnviroChemicals, Ltd.) was added and, after mixing, the mixture was placed in a heating reactor and heated at 180° C. for 30 minutes to obtain a sample. After cooling to room temperature, an aqueous 20% solution prepared from this sample was filtered to completely remove the activated carbon, and thus a soluble saccharide was obtained. The obtained soluble saccharide fraction was subjected to decolorization filtration with activated carbon, decolorization with an ion-exchange resin, and further evaporator concentration, and then dried. As a result, about 310 g of a product was obtained and the product had a dietary fiber content of 79.0%, a coloration degree of 0.26 (Bx.50), a whiteness of 94.5 (Bx.50), and an average molecular weight of 5,200.

The saccharide polycondensate produced in Example A10 was partially reacted at room temperature for 3 hours, using sodium cyanoborohydride, and the obtained sample had DE 0.

The saccharide polycondensate produced in Example A10 was partially subjected to resin fractionation using TOYO-PEARL HW-40S (measuring φ5.0×90 cm) as a carrier. As a result, the product obtained by removing a low molecular component of di- or lower saccharides had a dietary fiber content of 91.4%, and the product obtained by treating with α-amylase and glucoamylase, followed by resin fractionation had a dietary fiber content of 99.0%.

Example A11

Production (4) of Saccharide Polycondensate

To an aqueous Bx.65 solution prepared by mixing 120 g of a solid component of dextrin (Pinedex #1, manufactured by Matsutani Chemical Industry Co., Ltd.) with 280 g of a solid component of an anhydrous crystalline glucose (Medicalose, manufactured by Nihon Shokuhin Kako Co., Ltd.), 10% (per solid content) of activated carbon (Purified Shirasagi, manufactured by Japan EnviroChemicals, Ltd.) was added and, after mixing, the mixture was placed in a heating reactor and heated at 180° C. for 30 minutes to obtain a sample.

After cooling to room temperature, an aqueous 20% solution prepared from this sample was filtered to completely remove the activated carbon, and thus a soluble saccharide was obtained. The obtained soluble saccharide fraction was subjected to decolorization filtration with activated carbon, decolorization with an ion-exchange resin, and further evaporator concentration, and then dried. As a result, about 290 g of a product was obtained and the product had a dietary fiber content of 78.7%, a coloration degree of 0.45 (Bx.50), a whiteness of 89.0 (Bx.50), and an average molecular weight of 7,900.

The saccharide polycondensate produced in Example A11 was partially reacted at room temperature for 3 hours, using sodium cyanoborohydride, and the obtained sample had DE 0.1.

The saccharide polycondensate produced in Example A11 was partially subjected to resin fractionation using TOYO-PEARL HW-40S (measuring φ5.0×90 cm) as a carrier. As a result, the product obtained by removing a low molecular component of di- or lower saccharides had a dietary fiber content of 90.6%, and the product obtained by treating with α-amylase and glucoamylase, followed by resin fractionation had a dietary fiber content of 99.0%.

Example A12

Production (5) of Saccharide Polycondensate

To an aqueous Bx.90 solution prepared by mixing 30 kg of a solid component of maltooligosaccharide syrup (DE47, manufactured by Nihon Shokuhin Kako Co., Ltd.) with 70 kg of a solid component of glucose syrup (DE98, manufactured by Nihon Shokuhin Kako Co., Ltd.), 3% (per solid content) activated carbon (Steam Carbon (Food additive Grade), manufactured by FUTAMURA CHEMICAL CO., LTD.) was added and, after mixing, the mixture was placed in a heating reactor (continuous kneader) heated at 250° C. and then kneaded and heated to obtain a sample. The sample was received in a water bath, and an aqueous 30% solution prepared from this sample was filtered to completely remove the activated carbon, and thus a soluble saccharide was obtained. The obtained soluble saccharide fraction was subjected to decolorization filtration with activated carbon, decolorization with an ion-exchange resin, and further evaporator concentration, and then dried. As a result, about 90 kg of a product was obtained and the product had a dietary fiber content of 81.7% and a coloration degree of 0.14 (Bx.20).

[Solubility in Water]

Figure 7:
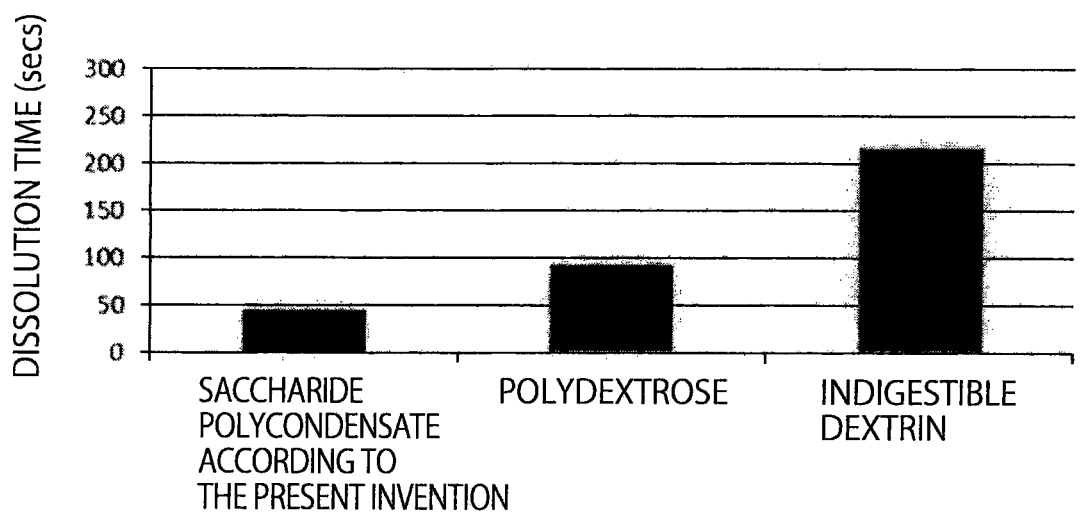
FIG. 7 is a diagram in which the solubility of the present saccharide polycondensate in water is compared with that of other indigestible dietary fibers in water.

A comparison was made between solubility of the saccharide polycondensate of Example A12 in water and solubility of various water-soluble dietary fibers (polydextrose, indigestible dextrin) in water. Upon testing, 200 g of distilled water was placed in a 300 ml-volume tall beaker and stirred (900 rpm) by a magnetic stirrer. Next, 20 g of each water-soluble dietary fiber material was placed in the beaker at a time, and then the time required to completely dissolve was measured. In order to eliminate a difference in solubility by a drying method, an aqueous 10% (w/w) solution prepared from each sample was dried using a freeze dryer and then a test was carried out using the sample. The test results are as shown in FIG. 7. As is apparent from FIG. 7, the saccharide polycondensate of the present invention is dissolved in water within less than half dissolution time as compared with other water-soluble dietary fibers.

[Solubility in Alcohol Solution]

Figure 8:
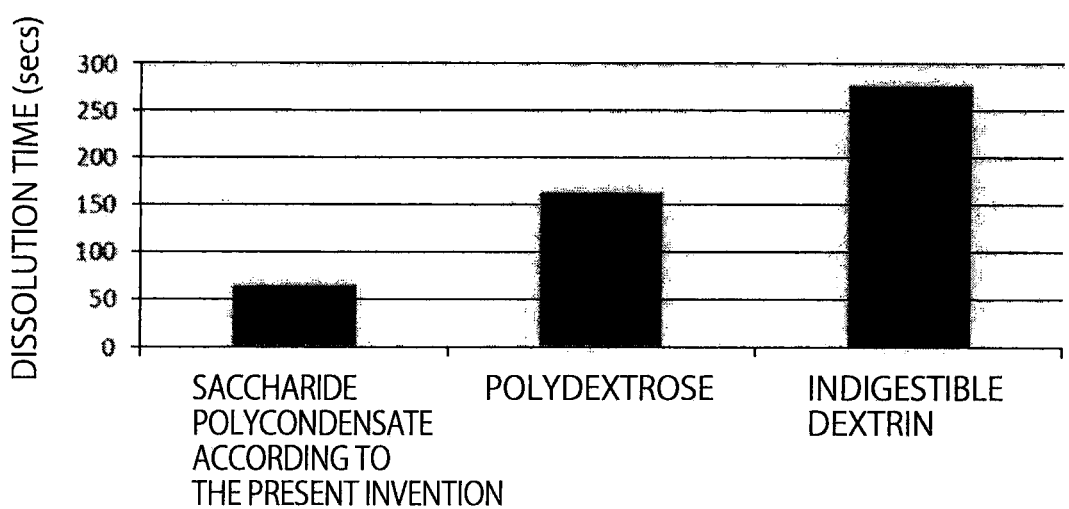
FIG. 8 is a diagram in which the solubility of the present saccharide polycondensate in ethanol is compared with that of other indigestible dietary fibers in ethanol.

Solubility of each of various water-soluble dietary fibers in an alcohol solution was compared by replacing "distilled water" used in a test method of solubility in water with 30% (v/v) ethanol. The test results are as shown in FIG. 8. As is apparent from FIG. 8, the saccharide polycondensate of the present invention is dissolved in an alcohol solution within less than half dissolution time as compared with other water-soluble dietary fibers.

In all water-soluble dietary fibers, a precipitate was not formed in a 30% (v/v) ethanol solution.

As mentioned above, the saccharide polycondensate of the present invention is excellent in solubility in water or an alcohol solution, and can decrease the dissolution time in the case of producing various food or beverage products, and thus enabling an improvement in production efficiency.

Sensory Evaluation Test

For the purpose of comparing various water-soluble dietary fibers, taste quality of an aqueous 10% solution was compared. Sensory evaluation of the aqueous solution thus prepared was carried out by 10 panelists, and taste quality was evaluated. Taste quality was evaluated by rating of excellent (A), satisfactory (B), ordinary (C), and poor (D), while flavor was evaluated by rating of excellent (A), satisfactory (B), ordinary (C), and poor (D). Polydextroses of commercially available water-soluble dietary fibers "Raites" (manufactured by Danisco Japan Ltd.) and "Raites II" (manufactured by Danisco Japan Ltd.), and indigestible dextrins "Pine Fiber" (manufactured by Matsutani Chemical Industry Co., Ltd.) and "Fibersol 2" (manufactured by Matsutani Chemical Industry Co., Ltd.) were respectively used as Comparative Examples. The evaluation results are as shown in Table 14.

TABLE 14

Sensory evaluation results

| | Taste quality | Flavor | Evaluation |
|---|---|---|---|
| Example A8 sample | B | A | Very slight sweetness and odorless |
| Example A9 sample | B | C | Very slight sweetness and slight caramelized flavor |
| Example A10 sample | A | A | Tasteless and odorless |
| Example A11 sample | A | A | Tasteless and odorless |
| Raites | D | D | Strong sourness, slight sweetness and strong caramelized flavor |
| Raites II | B | D | Slight sweetness and strong caramelized flavor |
| Pine Fiber | C | D | Very slight sweetness, strong powder odor and weak caramelized flavor |
| Fibersol 2 | B | D | Very slight sweetness, powder odor and weak caramelized flavor |

It was confirmed that the saccharide polycondensate thus obtained by the production method of the present invention is nearly tasteless and odorless similarly to a conventional dietary fiber. Namely, it was shown that the saccharide polycondensate obtained by the production method of the present invention can be used as an excipient and an extender of food or beverage products and pharmaceuticals without imparting off-flavor to the food or beverage products and pharmaceuticals to which the saccharide polycondensate is to be added.

Safety Test

Using the saccharide polycondensate of Example A12, the Ames test was carried out. Specifically, the test was carried out by a pre-incubation method under the condition that metabolic activation is performed or not, using *Salmonella typhimurium* TA100, TA1535, TA98, and TA1537, and *Escherichia coli* WP2 uvrA, so as to examine whether or not a water-soluble dietary fiber NSK-1100 has gene mutation capability. As a result, mutagenicity was not recognized in the saccharide polycondensate of Example A12.

Using mice, an acute toxicity test was carried out by orally administrating the saccharide polycondensate of Example A12. As a result, the saccharide polycondensate of the present invention is nontoxic and no fatal case was recognized in an administrable maximum dose, and a $LD_{50}$ value thereof was 10 g/kg (body weight of mouse) or more.

Digestibility Test

Using the saccharide polycondensate of Example A12, digestibility due to salivary amylase, simulated gastric juice, pancreatic amylase, and intestinal mucosal enzyme in a test tube was examined in accordance with the method of Okada et al. disclosed in Journal of Nutritional Science and Vitaminology, Vol. 43, pp23-29 (1990). Commercially available water-soluble dietary fibers (indigestible dextrin (Fibersol II: manufactured by Matsutani Chemical Industry Co., Ltd.) and polydextrose (Raites: manufactured by Danisco Japan Ltd.)) were used as controls. The results are as shown in Table 15.

TABLE 15

Results of digestibility test

| Digestive enzymes | Hydrolysis ratio (%) | | |
|---|---|---|---|
| | Present saccharide polycondensate | Fibersol II | Raites |
| Salivary amylase | 0 | 4.4 | 0 |
| Simulated gastric juice | 0 | 0.6 | 0 |
| Pancreatic amylase | 0.6 | 3.2 | 0 |
| Intestinal mucosal enzyme | 6.7 | 13.2 | 5.1 |

As is apparent from the results shown in Table 15, the saccharide polycondensate of the present invention was scarcely digested by salivary amylase and simulated gastric juice, and was hydrolyzed very slightly by pancreatic amylase. It has been found that a hydrolysis ratio of indigestible dextrin as a control due to an intestinal mucosal enzyme is 13.2%, whereas, a hydrolysis ratio of the saccharide polycondensate of the present invention is low such as 6.7%, and thus the saccharide polycondensate of the present invention is hard to be digested as compared with commercially available indigestible dextrin.

Structural Analysis

Regarding the saccharide polycondensates of Examples A8, A9, A10, A11, and A12, structural analysis due to the above-mentioned methylation analysis was carried out. The results are as shown in Table 16.

TABLE 16

Results of structural analysis

| Kind of partially methylated compound | Corresponding glucose residue | Existence ratio (area %) | | | | |
|---|---|---|---|---|---|---|
| | | Example A8 | Example A9 | Example A10 | Example A11 | Example A12 |
| 2,3,4,6-tetramethyl compound | Non-reducing terminal glucose residue | 53.0 | 49.9 | 45.3 | 39.9 | 47.0 |
| 2,4,6-trimethyl compound | 1,2-bound glucose residue | 4.3 | 7.7 | 5.9 | 5.3 | 5.6 |
| 3,4,6-trimethyl compound | 1,3-bound glucose residue | 5.9 | 6.2 | 4.7 | 6.3 | 7.2 |
| 2,3,6-trimethyl compound | 1,4-bound glucose residue | 8.2 | 8.0 | 15.8 | 23.8 | 13.1 |
| 2,3,4-trimethyl compound | 1,6-bound glucose residue | 22.5 | 17.9 | 18.2 | 14.5 | 17.2 |
| 2,3-, or 2,4-dimethyl compound | 1,3,6-bound, or 1,4,6-bound glucose residue | 6.1 | 10.3 | 10.2 | 10.3 | 9.8 |

As is apparent from the results shown in Table 16, main bond in the saccharide polycondensates of Examples A8, A9, A10, and A12 was 1,6-bond. Main bond in the saccharide polycondensate of Example A11 was 1,4-bond.

Example B

Application to High Intensity Sweetener-Containing Food or Beverage Product

Example B1

Study (1) of Effect on Food or Beverage Product of Saccharide Polycondensate

Sensory evaluation of an aqueous solution prepared by mixing the saccharide polycondensate (hereinafter sometimes referred simply to as a "present saccharide polycondensate") obtained in Example A12 with a high intensity sweetener (sucralose) was carried out. A test plot using the existing water-soluble dietary fiber materials, polydextrose (Raites: manufactured by Danisco Japan Ltd.) and indigestible dextrin (Pine Fiber (referred to as an indigestible dextrin A): manufactured by Matsutani Chemical Industry Co., Ltd., Fibersol 2 (referred to as an indigestible dextrin B): manufactured by Matsutani Chemical Industry Co., Ltd.) was also provided as Comparative Example. In the below-mentioned Examples, the above-mentioned commercially available water-soluble dietary fibers were used as comparative plots.

Each of the test materials prepared according to the formulations shown in Table 17 below was poured into 30 ml paper cups A to E in the amount of about 20 ml, and then a sensory evaluation test by a ranking method due to 10 volunteers (6 males, 4 females) was carried out with respect to three items of little bad taste (little aftertaste), tough body, and deliciousness. All test materials were subjected to sensory evaluation at room temperature. Since it may be difficult to perform complete ranking in view of contents of a test, same rank is possible in the evaluation. In that case, it was adjusted so that the total of ranks becomes 15 (Example 1 in which A: 1, B: 2.5, C: 2.5, D: 4, and E: 5 in case where B and C may be the same second rank; and Example 2 in which A: 2.5, B: 2.5, C: 2.5, D: 2.5, and E: 2.5 in case where there is no difference). Ranks are A, B, C, -, and D in the descending order and, in the case of the same rank, the rank was arranged in high rank. The sensory evaluation results are shown in Table 18.

TABLE 17

Formulation of Example B1

| | Test plot | Comparative plot 1 | Comparative plot 2 | Comparative plot 3 | Comparative plot 4 |
|---|---|---|---|---|---|
| Dietary fiber material | 0.50 | | | | |
| Raites | | 0.50 | | | |
| Pine Fiber | | | 0.50 | | |
| Fibersol II | | | | 0.50 | |
| Sucralose | 0.10 | 0.10 | 0.10 | 0.10 | 0.10 |
| Water | Balance | Balance | Balance | Balance | Balance |
| Total | 100.0 | 100.0 | 100.0 | 100.0 | 100.0 |

TABLE 18

Sensory evaluation results of Example B1

|  | Test plot | Comparative plot 1 | Comparative plot 2 | Comparative plot 3 | Comparative plot 4 |
|---|---|---|---|---|---|
| Little bad taste | A | — | D | C | B |
| Tough body | B | D | A | — | C |
| Deliciousness | A | C | — | D | B |

Table 18 revealed that bad taste and body are improved as compared with comparative plot 1 with no addition of a dietary fiber by mixing the present saccharide polycondensate with sucralose, and thus making it possible to obtain a food or beverage product having high taste quality. Furthermore, high effect was confirmed even by comparing with existing various dietary fibers (comparative plots 2 to 4) used as Comparative Examples. Comparative plot 2 containing polydextrose added therein had body but exerted weak effect of masking bad taste of sucralose, and exhibited inferior taste quality as compared with the test plot. Comparative plots 3 to 4 containing indigestible dextrin added therein had insufficient body imparted, and exhibited inferior taste quality as compared with the test plot.

Example B2

Study (2) of Effect on Food or Beverage Product of Saccharide Polycondensate

The addition amount of the present saccharide polycondensate was examined. Acesulfame K was used as high intensity sweetener. Each of the test materials prepared according to the formulations shown in Table 19 below was poured into 30 ml paper cups A to F in the amount of about 20 ml, and then a sensory evaluation test by a ranking method due to 10 volunteers (5 males, 5 females) was carried out with respect to three items of little bad taste (little aftertaste), tough body, and deliciousness. All test materials were subjected to sensory evaluation at room temperature. Since it may be difficult to perform complete ranking in view of contents of a test, same rank is possible in the evaluation. In that case, it was adjusted so that the total of ranks becomes 21 (Example 1 in which A: 1, B: 2.5, C: 2.5, D: 4, E: 5, and F: 6 in case where B and C may be the same second rank; and Example 2 in which A: 3.5, B: 3.5, C: 3.5, D: 3.5, E: 3.5, and F: 3.5 in case where there is no difference). Ranks are A, B, C, D, and E in the descending order and, in the case of the same rank, the rank was arranged in high rank. The sensory evaluation results are shown in Table 20.

TABLE 19

Formulation of Example B2

|  | Test plot 1 | Test plot 2 | Test plot 3 | Test plot 4 | Test plot 5 | Comparative plot |
|---|---|---|---|---|---|---|
| Present saccharide polycondensate | 0.01 | 0.10 | 1.00 | 10.00 | 25.00 | 0.00 |
| Acesulfame K | 0.67 | 0.67 | 0.67 | 0.67 | 0.67 | 0.67 |
| Water | Balance | Balance | Balance | Balance | Balance | Balance |
| Total | 100.0 | 100.0 | 100.0 | 100.0 | 100.0 | 100.0 |

TABLE 20

Sensory evaluation results of Example B2

|  | Test plot 1 | Test plot 2 | Test plot 3 | Test plot 4 | Test plot 5 | Comparative plot |
|---|---|---|---|---|---|---|
| Little bad taste | D | A | A | C | — | E |
| Tough body | D | C | A | B | C | E |
| Deliciousness | — | A | A | C | — | E |

Table 20 revealed that the addition amount of the present saccharide polycondensate is most suitably 0.1% to 10%. In test plot 1 in which the addition amount is 0.01% and test plot 5 in which the addition amount is 25%, both little bad taste and body exhibited high value as compared with comparative plot, but the effect was inferior as compared with other test plots.

Example B3

Study (1) of Effect on Food or Beverage Product of Saccharide Polycondensate in Presence of High Intensity Sweetener Sensory evaluation of an aqueous solution prepared by mixing the present saccharide polycondensate with aspartame was carried out. Each of the test materials prepared according to the formulations shown in Table 21 below was poured into 30 ml paper cups A to E in the amount of about 20 ml, and then a sensory evaluation test by a ranking method due to 10 volunteers (6 males, 4 females) was carried out with respect to three items of little bad taste (little aftertaste), tough body, and deliciousness. All test materials were subjected to sensory evaluation at room temperature. Since it may be difficult to perform complete ranking in view of contents of a test, same rank is possible in the evaluation. In that case, it was adjusted so that the total of ranks becomes 15 (Example 1 in which A: 1, B: 2.5, C: 2.5, D: 4, and E: 5 in case where B and C may be the same second rank; and Example 2 in which A: 2.5, B: 2.5, C: 2.5, D: 2.5, and E: 2.5 in case where there is no difference). Ranks are A, B, C, -, and D in the descending order and, in the case of the same rank, the rank was arranged in high rank. The sensory evaluation results are shown in Table 22.

TABLE 21

Formulation of Example B3

|  | Test plot | Comparative plot 1 | Comparative plot 2 | Comparative plot 3 | Comparative plot 4 |
|---|---|---|---|---|---|
| Present saccharide polycondensate | 0.50 |  |  |  |  |
| Polydextrose |  |  | 0.50 |  |  |
| Indigestible dextrin A |  |  |  | 0.50 |  |
| Indigestible dextrin B |  |  |  |  | 0.50 |
| Aspartame | 0.30 | 0.30 | 0.30 | 0.30 | 0.30 |
| Water | Balance | Balance | Balance | Balance | Balance |
| Total | 100.00 | 100.00 | 100.00 | 100.00 | 100.00 |

TABLE 22

Sensory evaluation results of Example B3

|  | Test plot | Comparative plot 1 | Comparative plot 2 | Comparative plot 3 | Comparative plot 4 |
|---|---|---|---|---|---|
| Little bad taste | B | — | E | C | A |
| Tough body | A | B | C | — | — |
| Deliciousness | A | C | A | E | — |

The same results as in Example 1 using sucralose as high intensity sweetener were obtained. Namely, it was shown that bad taste and body are remarkably improved as compared with comparative plot 1 with no addition of a dietary fiber by mixing the present saccharide polycondensate with sucralose, and thus making it possible to obtain a food or beverage product having high taste quality. Furthermore, apparently high effect was confirmed even by comparing with existing various dietary fibers (comparative plots 2 to 4) used as Comparative Examples. Comparative plot 2 containing polydextrose added therein exerted weak effect of masking bad taste peculiar to aspartame as compared with other test plots. Comparative plots 3 to 4 containing indigestible dextrin added therein had insufficient body imparted, and exhibited inferior taste quality as compared with the test plot.

Example B4

Study (2) of Effect on Food or Beverage Product of Saccharide Polycondensate in Presence of High Intensity Sweetener Sensory evaluation of an aqueous solution prepared by mixing the present saccharide polycondensate with neotame was carried out. Each of the test materials prepared according to the formulations shown in Table 23 below was poured into 30 ml paper cups A to E in the amount of about 20 ml, and then a sensory evaluation test by a ranking method due to 10 volunteers (7 males, 3 females) was carried out with respect to three items of little bad taste (little aftertaste), tough body, and deliciousness. All test materials were subjected to sensory evaluation at room temperature. Since it may be difficult to perform complete ranking in view of contents of a test, same rank is possible in the evaluation. In that case, it was adjusted so that the total of ranks becomes 15 (Example 1 in which A: 1, B: 2.5, C: 2.5, D: 4, and E: 5 in case where B and C may be the same second rank; and Example 2 in which A: 2.5, B: 2.5, C: 2.5, D: 2.5, and E: 2.5 in case where there is no difference). Ranks are A, B, C, -, and D in the descending order and, in the case of the same rank, the rank was arranged in high rank. The sensory evaluation results are shown in Table 24.

TABLE 23

Formulation of Example B4

|  | Test plot | Comparative plot 1 | Comparative plot 2 | Comparative plot 3 | Comparative plot 4 |
|---|---|---|---|---|---|
| Present saccharide polycondensate | 0.50 | | | | |
| Polydextrose | | | 0.50 | | |
| Indigestible dextrin A | | | | 0.50 | |
| Indigestible dextrin B | | | | | 0.50 |
| Neotame | 0.30 | 0.30 | 0.30 | 0.30 | 0.30 |
| Water | Balance | Balance | Balance | Balance | Balance |
| Total | 100.00 | 100.00 | 100.00 | 100.00 | 100.00 |

TABLE 24

Sensory evaluation results of Example B4

|  | Test plot | Comparative plot 1 | Comparative plot 2 | Comparative plot 3 | Comparative plot 4 |
|---|---|---|---|---|---|
| Little bad taste | A | — | C | D | B |
| Tough body | B | D | — | A | B |
| Deliciousness | A | D | — | C | B |

It was shown that bad taste and body are remarkably improved as compared with comparative plot 1 with no addition of a dietary fiber by mixing the present saccharide polycondensate with neotame, and thus making it possible to obtain a food or beverage product having high taste quality. Furthermore, high effect was confirmed even by comparing with existing various dietary fibers (comparative plots 2 to 4) used as Comparative Examples. Comparative plot 2 containing polydextrose added therein was not satisfactory in both effect of masking bad taste and imparting of body. Comparative plots 3 to 4 containing indigestible dextrin added therein could impart body, but was inferior in little different taste as compared with the test plot.

Example B5

Production Example (1) of Beverage (Carbonated Beverage)

Each of the test materials prepared according to the formulations shown in Table 25 below was poured into 30 ml paper cups A and B in the amount of about 20 ml, and then a sensory evaluation test by a ranking method due to 10 volunteers (7 males, 3 females) was carried out with respect to three items of little bad taste (little aftertaste), tough body, and deliciousness. All test materials were subjected to sensory evaluation at room temperature. Either one having higher rank was selected, and the test material supported by a large number of volunteers was rated A while the test material supported by a small number of volunteers was rated C, and the test material supported by the same number of volunteers was rated B. Sensory evaluation results are shown in Table 26.

TABLE 25

Formulation of Example B5

|  | Test plot | Comparative plot |
|---|---|---|
| Present saccharide polycondensate | 0.50 | |
| Citric acid | 0.15 | 0.15 |
| Ascorbic acid | 0.05 | 0.05 |
| Na citrate | 0.02 | 0.02 |
| Amino acid mix | 0.02 | 0.02 |
| Sucralose | 0.02 | 0.02 |
| Carbonated water | Balance | Balance |
| Grapefruit flavor | 0.01 | 0.01 |
| Total | 100.0 | 100.0 |

TABLE 26

Sensory evaluation results of Example B5

|  | Test plot | Comparative plot |
|---|---|---|
| Little bad taste | A | C |
| Tough body | A | C |
| Deliciousness | A | C |

A delicious carbonated beverage, which is excellent in both little bad taste and imparting of body as compared with comparative plot containing no dietary fiber added therein, was obtained by adding a dietary fiber (present saccharide polycondensate).

Example B6

Production Example (2) of Beverage (Apple Juice-Containing Beverage)

Each of the test materials prepared according to the formulations shown in Table 27 below was poured into 30 ml paper cups A and B in the amount of about 20 ml, and then a sensory evaluation test by a ranking method due to 10 volunteers (7 males, 3 females) was carried out with respect to three items of little bad taste (little aftertaste), tough body, and deliciousness. All test materials were subjected to sensory evaluation at room temperature. Either one having higher rank was selected, and the test material supported by a large number of volunteers was rated A while the test material supported by a small number of volunteers was rated C, and the test material supported by the same number of volunteers was rated B. Sensory evaluation results are shown in Table 28.

TABLE 27

Formulation of Example B6

|  | Test plot | Comparative plot |
|---|---|---|
| Present saccharide polycondensate | 0.50 | |
| 100% Apple juice | 30.00 | 30.00 |
| Ascorbic acid | 0.02 | 0.02 |
| Flavoring agent | 0.01 | 0.01 |
| Acesulfame K | 0.008 | 0.008 |
| Sucralose | 0.007 | 0.007 |
| Water | Balance | Balance |
| Total | 100.0 | 100.0 |

TABLE 28

Table 28: Sensory evaluation results of Example B6

|  | Test plot | Comparative plot |
|---|---|---|
| Little bad taste | A | C |
| Tough body | B | B |
| Deliciousness | A | C |

A delicious apple juice-containing beverage having bad taste reduced as compared with comparative plot containing no dietary fiber added therein was obtained by adding a dietary fiber (present saccharide polycondensate).

Example B7

Production Example (3) of Beverage (Coffee Beverage)

Each of the test materials prepared according to the formulations shown in Table 29 below was poured into 30 ml paper cups A and B in the amount of about 20 ml, and then a sensory evaluation test by a ranking method due to 10 volunteers (7 males, 3 females) was carried out with respect to three items of little bad taste (little aftertaste), tough body, and deliciousness. All test materials were subjected to sensory evaluation at room temperature. Either one having higher rank was selected, and the test material supported by a large number of volunteers was rated A while the test material supported by a small number of volunteers was rated C, and the test material supported by the same number of volunteers was rated B. Sensory evaluation results are shown in Table 30.

TABLE 29

Formulation of Example B7

|  | Test plot | Comparative plot |
|---|---|---|
| Present saccharide polycondensate | 0.50 | |
| Milk | 10.00 | 10.00 |
| Coffee extract | 3.50 | 35.0 |
| Sugar | 1.00 | 1.00 |
| Powdered skim milk | 1.00 | 1.00 |
| Emulsifier | 0.10 | 0.10 |
| Acesulfame K | 0.01 | 0.01 |
| Water | Balance | Balance |
| Total | 100.0 | 100.0 |

TABLE 30

Sensory evaluation results of Example B7

|  | Test plot | Comparative plot |
|---|---|---|
| Little bad taste | A | C |
| Tough body | A | C |
| Deliciousness | A | C |

A delicious coffee beverage, which is excellent in both little bad taste and imparting of body as compared with comparative plot containing no dietary fiber added therein, was obtained by adding a dietary fiber (present saccharide polycondensate).

Example B8

Production Example (4) of Beverage (Isotonic Sport Beverage)

Each of the test materials prepared according to the formulations shown in Table 31 below was poured into 30 ml paper cups A and B in the amount of about 20 ml, and then a sensory evaluation test by a ranking method due to 10 volunteers (7 males, 3 females) was carried out with respect to three items of little bad taste (little aftertaste), tough body, and deliciousness. All test materials were subjected to sensory evaluation at room temperature. Either one having higher rank was selected, and the test material supported by a large number of volunteers was rated A while the test material supported by a small number of volunteers was rated C, and the test material supported by the same number of volunteers was rated B. Sensory evaluation results are shown in Table 32.

TABLE 31

| Formulation of Example B8 | | |
| --- | --- | --- |
|  | Test plot | Comparative plot |
| Present saccharide polycondensate | 0.50 | 3.50 |
| Fructose-enriched liquid sugar | 3.50 | 3.50 |
| Amino acid mix | 3.50 | 0.20 |
| Citric acid | 0.20 | 1.00 |
| Flavoring agent | 1.00 | 0.10 |
| K chloride | 0.10 | 0.01 |
| Ascorbic acid | 0.01 | 0.01 |
| Salt | 0.01 | 0.01 |
| Sucralose | 0.01 | 0.01 |
| Water | Balance | Balance |
| Total | 100.0 | 100.0 |

TABLE 32

| Sensory evaluation results of Example B8 | | |
| --- | --- | --- |
|  | Test plot | Comparative plot |
| Little bad taste | A | C |
| Tough body | A | C |
| Deliciousness | A | C |

An isotonic sport beverage, which is excellent in both little bad taste and imparting of body as compared with comparative plot containing no dietary fiber added therein, was obtained by adding a dietary fiber (present saccharide polycondensate).

Example C

Application to Beer-Based Beverage

Example C1

Beer Flavored Alcoholic Beverage in which Saccharide Polycondensate is Added after Fermentation (Low-Malt Beer)

Dietary fiber-containing low-malt beer was prepared by adding 2 g of the saccharide polycondensate (hereinafter referred to as a present saccharide polycondensate) obtained in Example A12 to 98 g of commercially available low-malt beer. Also, dietary fiber-containing low-malt beer was prepared in the same manner as in the above production method, except that the present saccharide polycondensate was replaced by indigestible dextrin (Fibersol 2: manufactured by Matsutani Chemical Industry Co., Ltd.) or polydextrose (Raites: manufactured by Danisco Japan Ltd.) as Comparative Example. In the below-mentioned Examples and Test Examples, the above-mentioned commercially available products were used as the indigestible dextrin and polydextrose.

The obtained dietary fiber-containing low-malt beer was compared with low-malt beer containing no dietary fiber added therein, and then sensory evaluation was carried out based on evaluation criteria shown below.

[Evaluation]
A: Extremely preferable
B: Preferable
C: Equivalent to untreated plot
D: Not preferable The results of the above sensory evaluation are summarized in Table 33.

TABLE 33

| Sensory evaluation results of low-malt beer containing various water-soluble dietary fibers | | | |
| --- | --- | --- | --- |
|  | Present saccharide polycondensate | Ingestible dextrin | Polydextrose |
| Smoothness | B | C | D |
| Body | B | B | C |
| Flavor | A | C | B |
| Bitterness | B | C | B |
| Little off-flavor | A | C | D |
| Deliciousness | A | D | C |

The low-malt beer containing the present saccharide polycondensate added therein had rich body and fruity flavor as compared with the untreated plot, and exhibited enhanced smoothness of aftertaste. Furthermore, the low-malt beer was excellent in that it does not impart off-flavors such as sourness and sweetness as compared with low-malt beer containing other dietary fibers (indigestible dextrin, polydextrose) as Comparative Example.

Regarding indigestible dextrin and polydextrose, flavor deteriorates by masking flavor peculiar to a beer flavored alcoholic beverage using a dietary fiber, and flavor and taste quality are impaired by imparting off-flavor peculiar to a dietary fiber. It became apparent that the present saccharide polycondensate can impart smoothness and body, and can enhance a dietary fiber without impairing flavor and taste quality.

A bubble retention test of the dietary fiber-containing low-malt beer obtained by the above-mentioned test was carried out by the below-mentioned method.

The bubble retention test was carried out by a partially modified method of the Rudin method. A beer flavored alcoholic beverage, controlled to normal temperature by being left to stand at room temperature in advance, was poured into a 300 ml beaker, and then decarbonated by vigorously stirring for about 1 hour using a stirrer. To the decarbonated solution, various materials (2% (w/w)) were added. After dissolution, 100 ml of the solution was gently poured into a 500 ml measuring cylinder made of glass and then a carbonic acid gas was blown through a sintered metal filter, thereby causing frothing up to the graduation of 500 ml. Then, the time required for the upper surface of bubbles to fall down to the graduation of 400 ml was measured. The above test was repeated twice. The average value is shown in Table 34.

TABLE 34

Bubble retention test results

| Dietary fiber | No addition | Present saccharide polycondensate | Ingestible dextrin | Poly-dextrose |
|---|---|---|---|---|
| Bubble retention time (seconds) | 77.5 | 81 | 77 | 66.5 |

It was shown that bubble retention time of the low-malt beer containing the present saccharide polycondensate added therein is improved as compared with a dietary fiber non-addition plot and low-malt beer containing indigestible dextrin or polydextrose added therein as Comparative Example.

Example C2

Beer Flavored Alcoholic Beverage in which Saccharide Polycondensate is Added after Fermentation (Third Beer)

To 98 g of a commercially available third beer (effervescent liqueur), 2 g of various water-soluble dietary fiber materials were added and dissolved to prepare third beer containing a dietary fiber.

A comparison was made with third beer containing no dietary fiber added therein, and sensory evaluation was carried out based on evaluation criteria shown below.

[Evaluation]
A: Extremely preferable
B: Preferable
C: Equivalent to untreated plot
D: Not preferable The results of the above sensory evaluation are summarized in Table 35.

TABLE 35

Sensory evaluation results of third beer containing various water-soluble dietary fibers

| | Present saccharide polycondensate | Ingestible dextrin | Polydextrose |
|---|---|---|---|
| Smoothness | B | D | B |
| Body | B | B | C |
| Flavor | A | C | B |
| Bitterness | B | C | B |
| Little off-flavor | A | C | D |
| Deliciousness | A | B | C |

The same tendency as in the low-malt beer of Example C1 was also confirmed in the third beer. Namely, the third beer containing the present saccharide polycondensate added therein had rich body and fruity flavor as compared with the untreated plot, and exhibited enhanced smoothness of aftertaste. Furthermore, the third beer was excellent in that it does not impart off-flavors such as sourness and sweetness as compared with third beer containing other dietary fibers (indigestible dextrin, polydextrose) as Comparative Example.

Example C3

Beer Flavored Alcoholic Beverage in which Saccharide Polycondensate is Added Before Fermentation (Beer)

According to the formulation shown in Table 36, beer containing the present saccharide polycondensate added therein (the obtained beverage corresponds to "low-malt beer" under liquor tax law). A wort extract (Bavarian Pilsner: manufactured by Weyermann), hop (CSA P90: made in Czech), and yeast (dry yeast Saflager W34/70: manufactured by Fermentis) were used as the raw material shown in Table 36.

TABLE 36

Formulations of present saccharide polycondensate-containing beer and present saccharide polycondensate-free beer

| | Present saccharide polycondensate-containing beer | Present saccharide polycondensate-free beer |
|---|---|---|
| Wort extract | 177.42 g | 197.13 g |
| Present saccharide polycondensate | 14.96 g | 0 g |
| Hop | 1.80 g | 1.80 g |
| Yeast | 2.87 g | 2.87 g |
| Final weight* | 1,000 g | 1,000 g |

*The respective raw materials and water were combined to make 1,000 g of a final weight.

According to the above formulation, fermentation with yeast was carried out by maintaining at about 12° C. for 8 days, and a fermented liquid is subjected to an aging operation (second fermentation: maintained at about 15° C. for 4 days) to obtain beer containing the present saccharide polycondensate added therein.

The obtained beer containing the present saccharide polycondensate added therein was compared with beer containing no present saccharide polycondensate added therein, and then sensory evaluation was carried out. Namely, the obtained beer containing the present saccharide polycondensate added therein was compared with beer produced in the same manner, except that a dietary fiber (present saccharide polycondensate) is not contained as a raw material, and then sensory evaluation was carried out based on evaluation criteria shown below.

[Evaluation]
A: Extremely preferable
B: Preferable
C: Equivalent to untreated plot
D: Not preferable The results of the above sensory evaluation are summarized in Table 37.

TABLE 37

Sensory evaluation results of present saccharide polycondensate-containing beer

| Smoothness | B |
| Body | B |
| Flavor | A |
| Bitterness | B |
| Little off-flavor | B |
| Deliciousness | A |

The beer containing the present saccharide polycondensate added therein exhibited rich body and fruity flavor of hop as compared with beer of an untreated plot, and also had soft bitterness and aftertaste, and any off-flavor derived from a dietary fiber was not recognized.

Example C4

Beer Flavored Alcoholic Beverage in which Saccharide Polycondensate is Added Before Fermentation (Low-Malt Beer)

According to the formulation shown in Table 38, low-malt beer containing the present saccharide polycondensate added therein was produced. A wort extract (Bavarian Pilsner: manufactured by Weyermann), hop (CSA P90: made in Czech), yeast (dry yeast Saflager W34/70: manufactured by Fermentis), and starch syrup (High Maltose MC-55, manufactured by Nihon Shokuhin Kako Co., Ltd.) were used as beer raw materials shown in Table 38.

TABLE 38

Formulations of present saccharide polycondensate-containing low-malt beer and present saccharide polycondensate-free low-malt beer

|  | Present saccharide polycondensate-containing low-malt beer | Present saccharide polycondensate-free low-malt beer |
|---|---|---|
| Wort extract | 101.77 g | 101.77 g |
| Starch syrup | 74.77 g | 94.24 g |
| Present saccharide polycondensate | 14.96 g | 0 g |
| Hop | 1.80 g | 1.80 g |
| Yeast | 2.87 g | 2.87 g |
| Final weight* | 1,000 g | 1,000 g |

*The respective raw materials and water were combined to make 1,000 g of a final weight.

According to the above formulation, fermentation with yeast was carried out by maintaining at about 12° C. for 8 days, and a fermented liquid was subjected to an aging operation (second fermentation: maintained at about 14° C. for 6 days) to obtain low-malt beer. The obtained low-malt beer was compared with low-malt beer in which the present saccharide polycondensate is not added, and then sensory evaluation was carried out based on evaluation criteria shown below.

A: Extremely preferable
B: Preferable
C: Equivalent to untreated plot
D: Not preferable The results of the above sensory evaluation are summarized in Table 39.

TABLE 39

Sensory evaluation results of present saccharide polycondensate-containing low-malt beer

| Smoothness | C |
| Body | A |
| Flavor | B |
| Bitterness | B |
| Little off-flavor | A |
| Deliciousness | A |

The low-malt beer containing the present saccharide polycondensate added therein exhibited reduced outstanding sensation of sourness and bitterness as compared with an untreated plot, and also had soft body and smoothness free from off-flavor, and any off-flavor derived from a dietary fiber was not recognized.

Example D

Application to Food or Beverage Product

Example D1

Tea Containing Saccharide Polycondensate Added Therein

According to the formulation shown in Table 40, tea was prepared.

TABLE 40

Tea

|  | Comparative plot | Test plot |
|---|---|---|
| Tea extract liquid | 95.0 | 95.0 |
| Isomerized sugar | 5.0 | 5.0 |
| Present saccharide polycondensate | — | 10.0 |
| Dietary fiber | — | 8.2 |
| Dietary fiber per one meal (240 g) | 0.0 | 17.8 |

The tea containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the tea by the addition of the present saccharide polycondensate.

Example D2

Sweet Red-Bean Soup (with Rice Cake) Containing Saccharide Polycondensate Added Therein According to the formulation shown in Table 41, azuki-bean soup with rice cake was prepared.

TABLE 41

Sweet red-bean soup

|  | Comparative plot | Test plot |
|---|---|---|
| Strained bean paste | 14.6 | 14.6 |
| Granulated sugar | 16.6 | 16.6 |
| Salt | 0.1 | 0.1 |
| Processed starch | 0.5 | 0.5 |
| Water | 68.2 | 63.2 |
| Present saccharide polycondensate | — | 5.0 |
| Dietary fiber | 1.5 | 5.6 |
| Dietary fiber per one meal (240 g) | 3.6 | 13.4 |

The azuki-bean soup with rice cake, containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the azuki-bean soup with rice cake by the addition of the present saccharide polycondensate.

Example D3

Vanilla Shake Containing Saccharide Polycondensate Added Therein

According to the formulation shown in Table 42, water was mixed with powdered raw materials, followed by mixing and further dissolving by heating to 80° C. Butterfat was homogenized by a homogenizer, followed by aging at 5° C. until the next day. After freezing and rapid cooling to −40° C., the frozen product was well mixed to prepare vanilla shake.

TABLE 42

| Vanilla shake | | |
| --- | --- | --- |
|  | Comparative plot | Test plot |
| Powdered skim milk | 8.5 | 8.5 |
| Salt-free butter | 1.9 | 1.9 |
| Vegetable fat and oil | 1.5 | 1.5 |
| Emulsion stabilizer | 0.5 | 0.5 |
| Granulated sugar | 7.7 | 7.7 |
| Starch syrup | 13.6 | — |
| Stevia | — | 0.025 |
| Vanilla flavor | 0.05 | 0.05 |
| Water | 66.25 | 66.23 |
| Present saccharide polycondensate | — | 13.6 |
| Dietary fiber | 0.1 | 11.2 |
| Dietary fiber per one meal (240 g) | 0.2 | 16.8 |

The vanilla shake containing the present saccharide polycondensate (test plot) was free from bad taste and odor derived from the present saccharide polycondensate, and both appearance and flavor compared favorably with a control product (control plot). Furthermore, bad taste caused by the addition of stevia was masked. Therefore, it was shown that a dietary fiber can be given without impairing appearance and flavor of the vanilla shake cake by the addition of the present saccharide polycondensate.

Example D4

Ice Cream Containing Saccharide Polycondensate Added Therein

According to the formulation shown in Table 43, all raw materials were mixed and the mixture was heated to 70° C., followed by stirring using a homomixer. Butterfat was homogenized by a homogenizer, followed by aging for 1 day in a refrigerator. After freezing and rapid cooling to −40° C., the frozen product was rapidly cooled to prepare ice cream.

TABLE 43

| Ice cream | | |
| --- | --- | --- |
|  | Comparative plot | Test plot |
| Powdered skim milk | 9.5 | 9.5 |
| Salt-free butter | 6.00 | 6.0 |
| Purified coconut oil | 5.00 | — |
| Granulated sugar | 8.32 | — |
| Starch syrup | 9.40 | — |
| Aspartame | — | 0.02 |
| Acesulfame K | — | 0.01 |
| Flavoring agent | 2.00 | 2.00 |
| Emulsion stabilizer | 0.50 | 0.50 |
| Water | 59.28 | 59.28 |
| Present saccharide polycondensate | — | 22.7 |
| Dietary fiber | 0.1 | 18.7 |
| Dietary fiber per one meal (150 g) | 0.2 | 28.0 |

The ice cream containing the present saccharide polycondensate (test plot) was free from bad taste and odor derived from the present saccharide polycondensate, and both appearance and flavor compared favorably with a control product (control plot). Furthermore, bad taste caused by the addition of a high intensity sweetener was masked. Therefore, it was shown that a dietary fiber can be given without impairing appearance and flavor of the ice cream by the addition of the present saccharide polycondensate.

Example D5

Yogurt Beverage Containing Saccharide Polycondensate Added Therein

According to the formulation shown in Table 44, powdered skim milk containing 10% milk solid was fermented in advance to obtain an undiluted yogurt solution. Then, the undiluted yogurt solution other raw materials were mixed and dissolved, and the mixture was homogenized by a homogenizer to prepare yogurt beverage (drink yogurt).

TABLE 44

| Yogurt beverage | | |
| --- | --- | --- |
|  | Comparative plot | Test plot |
| Undiluted yogurt solution | 93.5 | 93.5 |
| Fructose | 6.0 | 6.0 |
| Stabilizer | 0.50 | 0.78 |
| Flavoring agent | 0.05 | 0.05 |
| Present saccharide polycondensate | — | 10.0 |
| Dietary fiber | 0.5 | 8.7 |
| Dietary fiber per one meal (240 g) | 1.2 | 18.9 |

The yogurt beverage containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the yogurt beverage by the addition of the present saccharide polycondensate.

Example D6

Yogurt Containing Saccharide Polycondensate Added Therein

According to the formulation shown in Table 45, raw materials were mixed, heated and then emulsified. After inoculation with 3% starter, the mixture was refrigerated when pH reached 4.6, and thus preparing yogurt.

TABLE 45

Yogurt

| | Comparative plot | Test plot |
|---|---|---|
| Milk | 57.0 | 57.0 |
| Powdered skim milk | 5.5 | 5.5 |
| Granulated sugar | 7.00 | — |
| Stevia | — | 0.04 |
| Processed starch | 1.50 | — |
| Pectin | 0.20 | 0.20 |
| Present saccharide polycondensate | — | 8.50 |
| Dietary fiber | 0.1 | 7.0 |
| Dietary fiber per one meal (150 g) | 0.1 | 14.7 |

The yogurt containing the present saccharide polycondensate (test plot) was free from bad taste and odor derived from the present saccharide polycondensate, and both appearance and flavor compared favorably with a control product (control plot). Furthermore, bad taste caused by the addition of a high intensity sweetener was masked. Therefore, it was shown that a dietary fiber can be given without impairing appearance and flavor of the yogurt by the addition of the present saccharide polycondensate.

Example D7

Candy Containing Saccharide Polycondensate Added Therein

According to the formulation shown in Table 46, raw materials other than a flavoring agent were dissolved in water and the solution was cooled to 80° C. after reaching 155° C. The flavoring agent was added, followed by mixing and further forming to prepare candy.

TABLE 46

Candy

| | Comparative plot | Test plot |
|---|---|---|
| Starch syrup | 49.4 | — |
| Citric acid | 0.5 | 0.5 |
| Flavoring agent | 0.10 | 0.10 |
| Sugar | 50.00 | 50.00 |
| Stevioside | — | 0.10 |
| Present saccharide polycondensate | — | 49.40 |
| Dietary fiber | 0.0 | 40.4 |
| Dietary fiber per one meal (12 g) | 0 | 4.8 |

The candy containing the present saccharide polycondensate (test plot) was free from bad taste and odor derived from the present saccharide polycondensate, and both appearance and flavor compared favorably with a control product (control plot). Furthermore, bad taste caused by the addition of a high intensity sweetener was masked. Therefore, it was shown that a dietary fiber can be given without impairing appearance and flavor of the candy by the addition of the present saccharide polycondensate.

Example D8

Chewing Gum Containing Saccharide Polycondensate Added Therein

According to the formulation shown in Table 47, raw materials other than a flavoring agent were placed in a pan and melted with heating, followed by well mixing. After cooling to 50° C. and saccharide was added, followed by mixing. The flavoring agent was added at 40° C., followed by mixing, forming and further cooling to prepare chewing gum.

TABLE 47

Chewing gum

| | Comparative plot | Test plot |
|---|---|---|
| Purified Cevian | 2.9 | 2.9 |
| Purified gum base | 28.6 | 28.6 |
| Glucose | 20.50 | 20.50 |
| Sugar | 28.30 | 28.30 |
| Flavoring agent | 0.80 | 0.80 |
| Peppermint | 0.80 | 0.80 |
| Wintergreen | 0.50 | 0.50 |
| Spearmint | 0.30 | 0.30 |
| Dextrin | 17.80 | — |
| Present saccharide polycondensate | — | 17.80 |
| Dietary fiber | 0.0 | 14.5 |
| Dietary fiber per one meal (4.5 g) | 0.0 | 0.7 |

The chewing gum containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the chewing gum by the addition of the present saccharide polycondensate.

Example D9

Custard Cream Containing Saccharide Polycondensate Added Therein

According to the formulation shown in Table 48, materials other than rapeseed oil were dispersed by a homomixer, followed by stirring, heating to 100° C. in an autoclave, maintaining for 5 minutes and further cooling to prepare custard cream.

TABLE 48

Custard cream

| | Comparative plot | Test plot |
|---|---|---|
| Processed starch | 4.5 | 4.5 |
| Corn starch | 1.00 | 1.00 |
| Powdered skim milk | 4.00 | 4.00 |
| Powdered whole milk | 2.50 | 2.50 |
| Whey protein | 1.50 | 1.50 |
| Salt | 0.03 | 0.03 |
| Sour agent | 0.06 | 0.06 |
| Polysaccharide thickener | 0.04 | 0.04 |
| Sugar | 14.00 | — |
| Starch syrup | 18.00 | — |
| Stevia | — | 0.13 |
| Frozen 20% sweetened egg yolk | 1.10 | 1.10 |
| Frozen egg white | 3.60 | 3.60 |
| Water | 37.20 | 37.20 |
| Rapeseed oil | 12.50 | 12.50 |
| Present saccharide polycondensate | — | 32.00 |
| Dietary fiber | 0.1 | 26.2 |
| Dietary fiber per one meal (240 g) | 0.2 | 62.9 |

The custard cream containing the present saccharide polycondensate (test plot) was free from bad taste and odor derived from the present saccharide polycondensate, and both appearance and flavor compared favorably with a control product (control plot). Furthermore, bad taste caused by the addition of a high intensity sweetener was masked.

Therefore, it was shown that a dietary fiber can be given without impairing appearance and flavor of the custard cream by the addition of the present saccharide polycondensate.

Example D10

Strawberry Jam Containing Saccharide Polycondensate Added Therein

According to the formulation shown in Table 49, raw materials other than pectin were mixed, and then the mixture was slightly crushed by a mixer and heated at low heat. After reaching Brix 60 during heating, pectin was added, followed by cooling to prepare strawberry jam.

TABLE 49

Strawberry jam

|  | Comparative plot | Test plot |
|---|---|---|
| Strawberry | 55.0 | 55.0 |
| Sugar | 30.00 | — |
| Starch syrup | 15 | — |
| Pectin | 0.30 | 0.30 |
| Citric acid | 0.11 | 0.11 |
| Stevia | — | 0.20 |
| Present saccharide polycondensate | — | 45.00 |
| Dietary fiber | 1.2 | 38.0 |
| Dietary fiber per one meal (30 g) | 0.4 | 25.0 |

The strawberry jam containing the present saccharide polycondensate (test plot) was free from bad taste and odor derived from the present saccharide polycondensate, and both appearance and flavor compared favorably with a control product (control plot). Furthermore, bad taste caused by the addition of a high intensity sweetener was masked. Therefore, it was shown that a dietary fiber can be given without impairing appearance and flavor of the strawberry jam by the addition of the present saccharide polycondensate.

Example D11

Blueberry Jam Containing Saccharide Polycondensate Added Therein

According to the formulation shown in Table 50, raw materials other than pectin were mixed, and then the mixture was slightly crushed by a mixer and heated at low heat. After reaching Brix 40 during heating, pectin was added, followed by cooling to prepare blueberry jam.

TABLE 50

Blueberry jam

|  | Comparative plot | Test plot |
|---|---|---|
| Blueberry | 41.8 | 41.8 |
| Granulated sugar | 15.40 | 15.40 |
| Starch syrup | 28.20 | — |
| Pectin | 1.10 | 1.10 |
| Citric acid | 0.30 | 0.30 |
| Water | 13.2 | 13.2 |
| Present saccharide polycondensate | — | 28.2 |
| Dietary fiber | 0.9 | 23.9 |
| Dietary fiber per one meal (30 g) | 0.6 | 16.8 |

The blueberry jam containing the present saccharide polycondensate (test plot) was free from bad taste and odor derived from the present saccharide polycondensate, and both appearance and flavor compared favorably with a control product (control plot). Furthermore, bad taste caused by the addition of a high intensity sweetener was masked. Therefore, it was shown that a dietary fiber can be given without impairing appearance and flavor of the blueberry jam by the addition of the present saccharide polycondensate.

Example D12

Sugar-Free Bean Jam Containing Saccharide Polycondensate Added Therein

According to the formulation shown in Table 51, adzuki beans were heated in a state where water just covers the beans to remove astringent taste, followed by draining. After the addition of water until water just covers the beans, and further heating for 120 minutes while pouring water, sugar was added and the mixture was boiled down until reaching Brix 60 to prepare a sugar-free bean jam.

TABLE 51

Sugar-free bean jam

|  | Comparative plot | Test plot |
|---|---|---|
| Azuki beans | 100 | 100 |
| Granulated sugar | 160 | 160 |
| Starch syrup | 24.00 | — |
| Stevia | — | 0.05 |
| Water | q.s. | q.s. |
| Present saccharide polycondensate | — | 24.0 |
| Dietary fiber | 0.9 | 20.5 |
| Dietary fiber per one meal (30 g) | 0.1 | 3.3 |

The sugar-free bean jam containing the present saccharide polycondensate (test plot) was free from bad taste and odor derived from the present saccharide polycondensate, and both appearance and flavor compared favorably with a control product (control plot). Furthermore, bad taste caused by the addition of a high intensity sweetener was masked. Therefore, it was shown that a dietary fiber can be given without impairing appearance and flavor of the sugar-free bean jam by the addition of the present saccharide polycondensate.

Example D13

Non-Oil Dressing Containing Saccharide Polycondensate Added Therein

According to the formulation shown in Table 52, liquid raw materials (thin soy sauce, sake, isomerized sugar, fermented seasoning, apple juice, water, grain vinegar, lemon juice, perilla extract, and present saccharide polycondensate) were mixed, and then powdered raw materials (salt, seafood extract, flavor broth, and bainiku (plum pulp)) were dissolved to prepare non-oil dressing.

TABLE 52

Non-oil dressing

|  | Comparative plot | Test plot |
|---|---|---|
| Thin soy sauce | 15 | 15 |
| Sake | 5 | 5 |
| Salt | 3 | 3 |

TABLE 52-continued

Non-oil dressing

| | Comparative plot | Test plot |
|---|---|---|
| Isomerized sugar | 25 | 5 |
| Fermented seasoning | 4.2 | 4.2 |
| Seafood extract | 2.5 | 2.5 |
| Apple juice | 2 | 2 |
| Flavor broth | 1 | 1 |
| Water | 16.5 | 16.5 |
| Grain vinegar | 22.5 | 22.5 |
| Lemon juice | 1.5 | 1.5 |
| Citric acid | 1.2 | 1.2 |
| Bainiku (plum pulp) | 0.5 | 0.5 |
| Perilla extract | 0.1 | 0.1 |
| Present saccharide polycondensate | — | 25 |
| Dietary fiber | 0.0 | 20.4 |
| Dietary fiber per one meal (20 g) | 0 | 3.9 |

The non-oil dressing containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the non-oil dressing by the addition of the present saccharide polycondensate.

Example D14

Mayonnaise Containing Saccharide Polycondensate Added Therein

According to the formulation shown in Table 53, powdered raw materials were dissolved in water and vinegar, and then egg yolk was mixed. The mixture was emulsified by adding salad oil little by little while stirring by a homomixer to prepare mayonnaise.

TABLE 53

Mayonnaise

| | Comparative plot | Test plot |
|---|---|---|
| Salad oil | 62.0 | 32.5 |
| Vinegar | 18.00 | 18.00 |
| Egg yolk | 16.50 | 10.00 |
| Salt | 3.00 | 3.00 |
| Sugar | 0.50 | 0.50 |
| Water | — | 11.00 |
| Present saccharide polycondensate | — | 25.00 |
| Dietary fiber | 0.0 | 20.4 |
| Dietary fiber per one meal (20 g) | 0 | 4.1 |

The mayonnaise containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the mayonnaise by the addition of the present saccharide polycondensate.

Example D15

Sweet Soy Glaze Containing Saccharide Polycondensate Added therein of Dango (Rice Dumpling)

According to the formulation shown in Table 54, a half amount of caster sugar, processed starch, and soup stock made from konbu, and the saccharide polycondensate were mixed, and then soy sauce, water, starch syrup, and mirin (sweet sake used as seasoning) were added, followed by heating. The mixture was heated for a while after it became sticky, and then the remaining sugar was mixed, followed by dissolving with heating. Heating was continued to prepare sweet soy glaze of dango (rice dumpling).

TABLE 54

Sweet soy glaze of dango (rice dumpling)

| | Comparative plot | Test plot |
|---|---|---|
| Caster sugar | 22.00 | 22.00 |
| Processed starch | 6.00 | 4.00 |
| Soup stock made from konbu | 0.20 | 0.20 |
| Soy sauce | 20.00 | 20.00 |
| Water | 31.80 | 25.80 |
| Starch syrup | 14.00 | — |
| Mirin (sweet sake used as seasoning) | 6.00 | 6.00 |
| Present saccharide polycondensate | — | 22.00 |
| Dietary fiber | 0.0 | 18.0 |
| Dietary fiber per one meal (20 g) | 0 | 4.9 |

The sweet soy glaze containing the present saccharide polycondensate (test plot) of dango (rice dumpling) was free from bad taste and odor derived from the present saccharide polycondensate, and both appearance and flavor compared favorably with a control product (control plot). Therefore, it was shown that a dietary fiber can be given without impairing appearance and flavor of the sweet soy glaze of dango by the addition of the present saccharide polycondensate.

Example D16

White Sauce Containing Saccharide Polycondensate Added Therein

According to the formulation shown in Table 55, weak flour and butter were heated to prepare roux in advance. Separately, whole milk powder, amino acid seasoning, salt, white pepper, processed starch, and present saccharide polycondensate were mixed, and then a pan containing milk and water was put on the fire. A mixture of powdered raw materials with roux was added, followed by dissolving with heating. The mixture was heated for a while after it became sticky to prepare white sauce.

TABLE 55

White sauce

| | Comparative plot | Test plot |
|---|---|---|
| Powdered whole milk | 5.00 | 5.00 |
| Consomme | 0.40 | 0.40 |
| Amino acid seasoning | 0.40 | 0.40 |
| Salt | 0.30 | 0.30 |
| White pepper | 0.01 | 0.01 |
| Milk | 20.00 | 20.00 |
| Water | 62.89 | 53.39 |
| Butter | 4.00 | 4.00 |
| Weak flour | 4.00 | 4.00 |
| Processed starch | 3.00 | 2.50 |
| Present saccharide polycondensate | — | 10.00 |
| Dietary fiber | 0.1 | 8.3 |
| Dietary fiber per one meal (150 g) | 0 | 12.4 |

The white sauce containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the white sauce containing the present saccharide polycondensate by the addition of the present saccharide polycondensate.

Example D17

Peanut Butter Containing Saccharide Polycondensate Added Therein

According to the formulation shown in Table 56, coconut oil was added to peanut and then the mixture was put in a food cutter until it becomes pasty. Then, starch syrup, peanut flavor, and present saccharide polycondensate were added, followed by stirring in the food cutter until the mixture becomes uniform to prepare peanut butter.

TABLE 56

| Peanut butter | | |
|---|---|---|
| | Comparative plot | Test plot |
| Peanut | 55.0 | 42.0 |
| Coconut oil | 25.0 | 20.0 |
| Starch syrup | 20.0 | 15.0 |
| Peanut flavor | 0.1 | 0.1 |
| Present saccharide polycondensate | — | 23.0 |
| Dietary fiber | 4.4 | 21.7 |
| Dietary fiber per one meal (20 g) | 0.9 | 4.3 |

The peanut butter containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the peanut butter by the addition of the present saccharide polycondensate.

Example D18

Corn Soup Containing Saccharide Polycondensate Added Therein

According to the formulation shown in Table 57, powdered skim milk, granulated sugar, starch, chicken powder, consomme soup, roasted chicken powder, emulsifier, and the saccharide polycondensate were mixed and then dissolved in warm water in advance. A solution prepared by dissolving milk and powdered raw materials in sweet corn puree was added, and then the mixture was put in a homogenizer. After heating and reaching 90° C., heating was stopped and a can was filled with the obtained product, and the can was subjected to retort sterilization to prepare corn soup.

TABLE 57

| Corn soup | | |
|---|---|---|
| | Comparative plot | Test plot |
| Sweet corn puree (Bx. 18) | 10.0 | 10.0 |
| Milk | 8.0 | 8.0 |
| Powdered whole milk | 2.0 | 2.0 |
| Granulated sugar | 3.0 | 3.0 |
| Starch | 2.0 | 2.0 |
| Consomme soup | 0.7 | 0.7 |

TABLE 57-continued

| Corn soup | | |
|---|---|---|
| | Comparative plot | Test plot |
| Chicken powder | 0.6 | 0.6 |
| Roasted chicken powder | 0.5 | 0.5 |
| Emulsifier | 0.1 | 0.1 |
| Water | 73.1 | 68.1 |
| Present saccharide polycondensate | — | 5.0 |
| Dietary fiber | 1.0 | 4.7 |
| Dietary fiber per one meal (150 g) | 1.5 | 7.1 |

The corn soup containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the corn soup by the addition of the present saccharide polycondensate.

Example D19

Curry Roux Containing Saccharide Polycondensate Added Therein

According to the formulation shown in Table 58, materials other than the present saccharide polycondensate were mixed and a 10% by weight solution prepared by dissolving the present saccharide polycondensate was subjected to spray granulation and further forming by compacting to prepare cubic curry roux.

TABLE 58

| Curry roux | | |
|---|---|---|
| | Comparative plot | Test plot |
| Wheat flour | 30.0 | 30.0 |
| Curry powder | 7.0 | 7.0 |
| Savory herbs and meat extract | 25.0 | 25.0 |
| Meat extract | 25.0 | 25.0 |
| Salt | 5.0 | 5.0 |
| Sugar | 5.0 | 5.0 |
| Chutney | 5.0 | 5.0 |
| Monosodium glutamate | 3.00 | 3.00 |
| Starch | 0.50 | — |
| Present saccharide polycondensate | — | 5.00 |
| Dietary fiber | 0.6 | 4.4 |
| Dietary fiber per one meal (12 g) | 0.1 | 0.5 |

The curry roux containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the curry roux by the addition of the present saccharide polycondensate.

Example D20

Bread Containing Saccharide Polycondensate Added Therein

According to the formulation shown in Table 59, dough was well kneaded, fermented and then baked to prepare bread.

TABLE 59

Bread

| | Comparative plot | Test plot |
|---|---|---|
| Wheat flour | 100.0 | 100.0 |
| Water | 68.00 | 68.00 |
| Yeast | 3.00 | 3.00 |
| Salt | 2.00 | 2.00 |
| Sugar-mixed isomerized sugar | 13.00 | — |
| Powdered skim milk | 2.00 | 2.00 |
| Fat and oil | 6.00 | 6.00 |
| Present saccharide polycondensate | — | 13.00 |
| Dietary fiber | 1.4 | 12.0 |
| Dietary fiber per one meal (180 g) | 1.3 | 11.4 |

The bread containing the present saccharide polycondensate (test plot) was free from bad taste and odor derived from the present saccharide polycondensate, and both appearance and flavor compared favorably with a control product (control plot). Furthermore, bad taste caused by the addition of a high intensity sweetener was masked. Therefore, it was shown that a dietary fiber can be given without impairing appearance and flavor of the bread by the addition of the present saccharide polycondensate.

Example D21

Spaghetti Containing Saccharide Polycondensate Added Therein

According to the formulation shown in Table 60, dough was well kneaded and then spaghetti was prepared while adding water little by little.

TABLE 60

Spaghetti

| | Comparative plot | Test plot |
|---|---|---|
| Wheat flour | 100.0 | 100.0 |
| Water | 30.00 | 25.00 |
| Present saccharide polycondensate | — | 5.00 |
| Dietary fiber | 2.1 | 6.2 |
| Dietary fiber per one meal (200 g) | 3.2 | 9.5 |

The spaghetti containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the spaghetti by the addition of the present saccharide polycondensate.

Example D22

Omelette Containing Saccharide Polycondensate Added Therein

According to the formulation shown in Table 61, the present saccharide polycondensate was dissolved in milk and then other raw materials were mixed with egg. After oiling a frying pan using salad oil, the mixture was baked to prepare omelette.

TABLE 61

Omelette

| | Comparative plot | Test plot |
|---|---|---|
| Whole egg | 100.0 | 100.0 |
| Milk | 30.00 | 30.00 |
| Salt | 1.00 | 1.00 |
| Pepper | 0.20 | 0.20 |
| Butter | 5.00 | 5.00 |
| Present saccharide polycondensate | — | 15.00 |
| Dietary fiber | 0.0 | 12.3 |
| Dietary fiber per one meal (100 g) | 0 | 8.1 |

The omelette containing the present saccharide polycondensate (test plot) was free from bad taste and odor derived from the present saccharide polycondensate, and both appearance and flavor compared favorably with a control product (control plot). Therefore, it was shown that a dietary fiber can be given without impairing appearance and flavor of the omelette by the addition of the present saccharide polycondensate.

Example D23

Use as Powdered Base

To 100 g of green tea, 300 g of an aqueous 30% ethanol solution at 65° C. was added. After extracting at 60° C. for 60 minutes, solid-liquid separation was carried out. A solution having an ethanol concentration of 8.0%, prepared by adding 730 g of water to 270 g of the obtained extract liquid was mixed with 200 g of the present saccharide polycondensate, and then the mixture was spray-dried to obtain 200 g of green tea extract powder having an ethanol concentration of 0.9 (W/W) %. The obtained green tea extract powder is a material which is excellent in solubility and easy to handle, and also has moderate bitterness and satisfactory balance between flavor and taste.

Example D24

Liquid Food Containing Saccharide Polycondensate Added Therein

Protein (casein sodium) (4% by weight), 0.5% by weight of xanthan gum, and 20% by weight of the present saccharide polycondensate were dissolved in tap water at 55 to 60° C. using Three-One Motor (700 rpm). After confirming that they have been completely dissolved, a solution prepared by dissolving 0.09% by weight of potassium hydroxide, 0.09% by weight of citric acid, 0.07% by weight of sodium chloride, 0.01% by weight of a calcium salt, and 0.005% by weight of a magnesium salt in tap water was added, followed by mixing. To the mixture, 3% by weight of fat and oil, organic acid monoglyceride, and a polyglycerin fatty acid ester were added, and then the mixture was put in a homomixer (8,000 rpm 10 minutes). At this time, pH was measured and adjusted within a range of pH 6.8 to 7.2. After heating again to 60° C. by double boiling, the mixture was put in a homogenizer (500 kgf·cm²), bottled and then subjected to retort sterilization (121° C., F15). The obtained food compared favorably with a conventional liquid food.

Example D25

Use as Cooked Rice Loosening Agent

To 300 g of polished rice, 440 g of water was added and 3% by weight of the present saccharide polycondensate was dissolved, and then rice cooking was carried out by a rice cooker. The obtained cooked rice was enriched with a dietary fiber as compared with cooked rice without addition, and also loosening effect was confirmed. Taste quality and flavor compared favorably with cooked rice without addition.

Example E

Application to Feed

Example E1

Dog Food Containing Saccharide Polycondensate Added Therein

According to the formulation shown in Table 62, dog food was prepared.

TABLE 62

| Dog food | | |
|---|---|---|
| | Comparative plot | Test plot |
| Corn | 25.0 | 25.0 |
| Wheat flour | 22.00 | 22.00 |
| Chicken and chicken meal | 23.00 | 23.00 |
| Soybean meal | 14.40 | 14.40 |
| Fish powder | 3.30 | 3.30 |
| Wheat germ | 2.90 | 2.90 |
| Fermenting dry yeast | 0.50 | 0.50 |
| Chicken fat and oil | 3.00 | 3.00 |
| Vitamins and minerals | 5.90 | 5.90 |
| Present saccharide polycondensate | — | 10.00 |
| Dietary fiber | 4.7 | 12.9 |

The dog food containing the present saccharide polycondensate (test plot) had quality identical to that of a control product (control plot). It was shown that a dietary fiber can be given without impairing quality of the dog food by the addition of the present saccharide polycondensate.

Example E2

Cat Food Containing Saccharide Polycondensate Added Therein

According to the formulation shown in Table 63, cat food was prepared.

TABLE 63

| Cat food | | |
|---|---|---|
| | Comparative plot | Test plot |
| Corn | 28.4 | 28.4 |
| Wheat flour | 27.30 | 27.30 |
| Fermenting dry yeast | 3.30 | 3.30 |
| Wheat germ | 3.30 | 3.30 |
| Soybean meal | 16.40 | 16.40 |
| Fish powder | 0.50 | 0.50 |
| Chicken and chicken meal | 18.60 | 18.60 |
| Vitamins and minerals | 2.20 | 2.20 |
| Present saccharide polycondensate | — | 10.00 |
| Dietary fiber | 5.4 | 13.6 |

The cat food containing the present saccharide polycondensate (test plot) had quality identical to that of a control product (control plot). It was shown that a dietary fiber can be given without impairing quality of the cat food by the addition of the present saccharide polycondensate.

Example E3

Livestock Feed Containing Saccharide Polycondensate Added Therein

According to the formulation shown in Table 64, livestock feed was prepared.

TABLE 64

| Livestock feed | | |
|---|---|---|
| | Comparative plot | Test plot |
| Corn | 64.4 | 64.4 |
| Soybean meal | 28.09 | 28.09 |
| Beef tallow | 3.00 | 3.00 |
| Limestone | 0.12 | 0.12 |
| Calcium phosphate | 1.86 | 1.86 |
| Molasses | 2.00 | 2.00 |
| Salt | 0.20 | 0.20 |
| Mixture of minerals | 0.12 | 0.12 |
| Mixture of vitamins | 0.10 | 0.10 |
| Antioxidant | 0.05 | 0.05 |
| Antibiotic agent | 0.10 | 0.10 |
| Present saccharide polycondensate | — | 10.00 |
| Dietary fiber | 7.0 | 15.1 |

The livestock feed containing the present saccharide polycondensate (test plot) had quality identical to that of a control product (control plot). It was shown that a dietary fiber can be given without impairing quality of the livestock feed by the addition of the present saccharide polycondensate.

The invention claimed is:

1. A method for producing a saccharide polycondensate composition, which comprises the steps of:
providing one or more saccharides or derivatives thereof, said derivatives being selected from the group consisting of saccharic acids, sugar alcohols, amino sugars, etherified sugars, halogenated sugars, and phosphorylated sugars;
mixing the one or more saccharides or derivatives thereof with a catalyst consisting essentially of activated carbon to yield a mixture; and
polycondensing the one or more saccharides or derivatives thereof using the activated carbon as the sole catalyst by heating the mixture at a predetermined temperature wherein the one or more saccharides or derivatives thereof undergo polycondensation polymerization to form glycosidic linkages and produce the saccharide polycondensate composition, wherein the content of a dietary fiber in the saccharide polycondensate composition is 30% by weight or more and wherein the absorbance at 420 nm ($OD_{420}$) in an aqueous 20% (w/w) solution of the saccharide polycondensate is in a range of 0 to 5.0.

2. The method according to claim 1, wherein the saccharide is selected from a monosaccharide, an oligosaccharide, and a polysaccharide.

3. The method according to claim 1, wherein the polycondensation polymerization is carried out under a vacuum condition.

4. The method according to claim 1, wherein the step of polycondensing the one or more saccharides or derivatives thereof is carried out under the predetermined temperature of 170° C. to 280° C.

5. The method according to claim 1, wherein the saccharide polycondensate composition comprises a saccharide polycondensate with a polymerization degree of 3 or more and a saccharide with a polymerization degree of less than 3.

6. The method according to claim 5, wherein the content of a dietary fiber in the saccharide polycondensate composition is 30% by weight or more and wherein the absorbance at 420 nm ($OD_{420}$) in an aqueous 20% (w/w) solution of the saccharide polycondensate is in a range of 0 to 2.0.

7. The method according to claim 1 further comprising the step of reducing the saccharide polycondensate in said saccharide polycondensate composition to produce a reduced product of the saccharide polycondensate, wherein the step of reducing the saccharide polycondensate comprises reducing terminal glucosyl groups of the saccharide polycondensate into hydroxyl groups.

8. A method for producing a saccharide polycondensate, which comprises the steps of:
   providing one or more saccharides or derivatives thereof, said derivatives being selected from the group consisting of saccharic acids, sugar alcohols, amino sugars, etherified sugars, halogenated sugars, and phosphorylated sugars;
   mixing the one or more saccharides or derivatives thereof with a catalyst consisting essentially of activated carbon to yield a mixture; and
   polycondensing the one or more saccharides or derivatives thereof using the activated carbon as the sole catalyst by heating the mixture at a predetermined temperature wherein the one or more saccharides or derivatives thereof undergo polycondensation polymerization to form glycosidic linkages and produce the saccharide polycondensate.

9. The method according to claim 8, wherein the step of polycondensing is carried out under a vacuum condition.

10. The method according to claim 8, wherein the step of polycondensing the one or more saccharides or derivatives thereof is carried out under the predetermined temperature of 170° C. to 280° C.

11. The method according to claim 1, wherein the mixture consists of the activated carbon and the one or more saccharides or derivatives thereof.

12. The method according to claim 8, wherein the mixture consists of the activated carbon and the one or more saccharides or derivatives thereof.

13. The method according to claim 1, wherein the step of polycondensing the one or more saccharides or derivatives thereof is carried out under the predetermined temperature of 170° C. to 280° C. and wherein the mixture consists of the activated carbon and the one or more saccharides or derivatives thereof.

14. The method according to claim 8, wherein the step of polycondensing the one or more saccharides or derivatives thereof is carried out under the predetermined temperature of 170° C. to 280° C. and wherein the mixture consists of the activated carbon and the one or more saccharides or derivatives thereof.

* * * * *